(12) United States Patent
Findikoglu et al.

(10) Patent No.: US 12,158,449 B2
(45) Date of Patent: Dec. 3, 2024

(54) COMBINED ANALYTIC TECHNIQUE FOR DIFFERENTIATING CHANGES TO STRUCTURES USING ACOUSTIC SIGNALS

(71) Applicants: Chevron U.S.A. Inc., San Ramon, CA (US); Triad National Security, LLC, Los Alamos, NM (US)

(72) Inventors: Alp Tugrul Findikoglu, Los Alamos, NM (US); Daniel Robert Chapman, San Ramon, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 282 days.

(21) Appl. No.: 17/620,322

(22) PCT Filed: Jun. 18, 2019

(86) PCT No.: PCT/US2019/037751
§ 371 (c)(1),
(2) Date: Dec. 17, 2021

(87) PCT Pub. No.: WO2020/256707
PCT Pub. Date: Dec. 24, 2020

(65) Prior Publication Data
US 2022/0268744 A1    Aug. 25, 2022

(51) Int. Cl.
*G01N 29/44*    (2006.01)
*G01N 29/07*    (2006.01)
(Continued)

(52) U.S. Cl.
CPC ......... *G01N 29/4427* (2013.01); *G01N 29/07* (2013.01); *G01N 29/12* (2013.01);
(Continued)

(58) Field of Classification Search
CPC .... G01N 29/4427; G01N 29/07; G01N 29/12; G01N 29/46; G01N 29/50; G01N 33/20; G01N 2291/102
(Continued)

(56) References Cited

U.S. PATENT DOCUMENTS 4,352,292 A * 10/1982 Madigosky .......... G01N 33/445
    73/575
4,623,468 A    11/1986 Lepain
(Continued)

FOREIGN PATENT DOCUMENTS

CN        113325075 A  *  8/2021
WO        2017099852       6/2017
WO    WO-2017099852 A1 *  6/2017  ............... G01F 1/66

OTHER PUBLICATIONS

WO2017099852 (Year: 2017).*
(Continued)

*Primary Examiner* — Peter J Macchiarolo
*Assistant Examiner* — Monica S Young
(74) *Attorney, Agent, or Firm* — ESPLIN & ASSOCIATES, PC

(57) ABSTRACT

Combinations of multiple analytic techniques may be used to identify changes to a structure based on changes in characteristics of acoustic signals traveling along the structure. Acoustic signals traveling along the structure may be monitored to detect changes in characteristics of the acoustic signal from baseline signal characteristics. The changes in characteristics of the acoustic signals may be processed using multiple analytic techniques to provide analyses of the change in time-domain, in frequency-domain, and in mixed time-frequency-domain. The change to the structure may be
(Continued)

identified based on a combination of the results of the analysis in time-domain, in frequency-domain, and in mixed time-frequency-domain.

14 Claims, 24 Drawing Sheets

(51) Int. Cl.
*G01N 29/12* (2006.01)
*G01N 29/46* (2006.01)
*G01N 29/50* (2006.01)
*G01N 33/20* (2019.01)

(52) U.S. Cl.
CPC ............ *G01N 29/46* (2013.01); *G01N 29/50* (2013.01); *G01N 33/20* (2013.01); *G01N 2291/102* (2013.01)

(58) Field of Classification Search
USPC .......................................................... 73/579
See application file for complete search history.

(56) References Cited

U.S. PATENT DOCUMENTS

| | | | |
|---|---|---|---|
| 4,890,055 A | 12/1989 | Van Broekhoven | |
| 5,526,689 A | 6/1996 | Coulter | |
| 5,987,990 A | 11/1999 | Worthington | |
| 7,307,914 B1 | 12/2007 | Carter | |
| 8,176,783 B2* | 5/2012 | Sinha | G01N 29/348 73/579 |
| 8,225,665 B2 | 7/2012 | Geir | |
| 9,558,762 B1* | 1/2017 | Sieracki | G10L 15/00 |
| 9,625,603 B2* | 4/2017 | Stolpman | G01V 3/34 |
| 9,632,062 B2 | 4/2017 | Tanaka | |
| 9,778,389 B2* | 10/2017 | Stolpman | H04B 13/02 |
| 10,473,625 B2 | 11/2019 | Findikoglu | |
| 10,585,069 B2 | 3/2020 | Findikoglu | |
| 10,996,203 B2 | 5/2021 | Findikoglu | |
| 2002/0058871 A1* | 5/2002 | Oravecz | G01N 29/46 600/437 |
| 2002/0149488 A1* | 10/2002 | Kechter | G01M 3/243 702/39 |
| 2007/0017800 A1 | 1/2007 | Cetinkaya | |
| 2007/0072137 A1 | 3/2007 | Peluso | |
| 2007/0104335 A1* | 5/2007 | Shi | H04R 3/02 381/83 |
| 2009/0150094 A1 | 6/2009 | Van Velsor | |
| 2009/0234590 A1* | 9/2009 | McNealy | G01N 27/82 324/237 |
| 2010/0018311 A1 | 1/2010 | Batzinger | |
| 2010/0079258 A1 | 4/2010 | Ihn | |
| 2010/0278008 A1 | 11/2010 | Ammar | |
| 2010/0319455 A1* | 12/2010 | Ihn | G01N 29/44 73/603 |
| 2011/0301882 A1 | 12/2011 | Andersen | |
| 2012/0055253 A1 | 3/2012 | Sinha | |
| 2012/0055264 A1 | 3/2012 | Sinha | |
| 2015/0053009 A1* | 2/2015 | Yan | G01N 29/46 73/598 |
| 2015/0212048 A1 | 7/2015 | Ganesan | |
| 2017/0076563 A1 | 3/2017 | Guerriero | |
| 2018/0231501 A1* | 8/2018 | Findikoglu | G01N 29/4472 |
| 2018/0292356 A1 | 10/2018 | Findikoglu | |
| 2020/0191754 A1* | 6/2020 | Findikoglu | G01N 29/223 |
| 2020/0378825 A1* | 12/2020 | Chen | G01V 1/30 |

OTHER PUBLICATIONS

Taeho Ju and Alp T. Findikoglu; "Ultrasonic Testing of Mechanical Changes in aWater-Filled Pipe with Multi-Mode and Broadband Signals and Two-Level Compensation"; MDPI, Sensors; 2022, 22, 8647 (p. 1-15).
PCT International Search Report and Written Opinion, International Application No. PCT/US2019/037751, dated Aug. 27, 2019, 8 pages.

* cited by examiner

COMBINED ANALYTIC TECHNIQUE FOR DIFFERENTIATING CHANGES TO STRUCTURES USING ACOUSTIC SIGNALS

ACKNOWLEDGEMENT OF GOVERNMENT SUPPORT

This invention was made with United States (U.S.) government support under Contract No. DE-AC52-06NA25396 awarded by the U.S. Department of Energy. The U.S. government has certain rights in the invention.

PARTIES TO JOINT RESEARCH AGREEMENT

The research work described here was performed under a Cooperative Research and Development Agreement (CRADA) between Los Alamos National Laboratory (LANL) and Chevron under the LANL-Chevron Alliance, CRADA number LA05C10518.

TECHNICAL FIELD

The present disclosure relates generally to the field of identifying changes to structures using acoustic signals.

BACKGROUND

Changes to a structure may result in changes to characteristics of acoustic signals traveling along the structure. A single analytic technique may be insufficient to differentiate between different changes and/or different sources of changes to the structure.

SUMMARY

This disclosure relates to combined analytic technique for differentiating changes to structures using acoustic signals. An acoustic transmission transducer may transmit one or more acoustic signals along a structure. An acoustic reception transducer may receive the acoustic signal(s) after the acoustic signal(s) have traveled along at least a portion of the structure. The acoustic reception transducer may generate output signals conveying signal characteristics of the received acoustic signal(s). The output signals may be monitored for a change in the signal characteristics of the received acoustic signal(s) from baseline signal characteristics. The change in the signal characteristics of the received acoustic signal(s) may be caused by a change to the structure. The change in the signal characteristics of the received acoustic signal(s) may be analyzed based on a set of analytic techniques and/or other information. The set of analytic techniques may provide analyses of the change in the signal characteristics of the received acoustic signal(s) in time-domain, in frequency-domain, in mixed time-frequency-domain, and/or other domains. The change to the structure may be identified based on the analyses of the change in the signal characteristics of the received acoustic signal(s) in time-domain, in frequency-domain, in mixed time-frequency-domain, and/or in other domains, and/or other information.

A system that identifies changes to a structure may include one or more electronic storage, one or more acoustic transmission transducers, one or more acoustic reception transducers, one or more processors and/or other components. The electronic storage may store information relating to acoustic signals, information relating to transmission of acoustic signals, information relating to reception of acoustic signals, information relating to output signals, information relating to signal characteristics, information relating to changes in signal characteristics, information relating to baseline signal characteristics, information relating to structures, information relating to changes to structures, information relating to analytic techniques, information relating to analyses of change in signal characteristics in time-domain, in frequency-domain, and/or in mixed time-frequency-domain, information relating to identification of changes to structures, and/or other information.

The acoustic transmission transducer(s) may be configured to transmit one or more acoustic signals along a structure. In some implementations, one or more amplitude-time frequency characteristics of the acoustic signal(s) may be tuned for one or more structures and/or one or more changes to the structure(s). In some implementation, a structure may include a metallic, rigid structure and/or other structure. A metallic, rigid structure may include a pipe, a vessel, or a container, and/or other metallic, rigid structure.

The acoustic reception transducer(s) may be configured to receive the acoustic signal(s) after the acoustic signal(s) have traveled along at least a portion of the structure. The acoustic reception transducer(s) may be configured to generate output signals conveying signal characteristics of the received acoustic signal(s) and/or other information.

The processor(s) may be configured by machine-readable instructions. Executing the machine-readable instructions may cause the processor(s) to facilitate identifying changes to a structure using acoustic signals. The machine-readable instructions may include one or more computer program components. The computer program components may include one or more of a monitor component, an analysis component, an identification component, and/or other computer program components.

The monitor component may be configured to monitor the output signals for a change in the signal characteristics of the received acoustic signal from baseline signal characteristics. The change in the signal characteristics of the received acoustic signal may include one or more differences between the signal characteristics of the received acoustic signal and the baseline signal characteristics. The change in the signal characteristics of the received acoustic signal may be caused by one or more changes to the structure.

The analysis component may be configured to analyze the change in the signal characteristics of the received acoustic signal based on a set of analytic techniques and/or other information. The set of analytic techniques may provide analyses of the change in the signal characteristics of the received acoustic signal in time-domain, in frequency-domain, in mixed time-frequency-domain, and/or in other domains. In some implementations, the set of analytic techniques may include two or more of a short-time-Fourier-transform difference maximum technique, a time-integrated mean technique, a time-integrated standard deviation technique, an auto-correlation mean technique, an auto-correlation standard deviation technique, a time-shift mean technique, a time-shift standard deviation technique, a piecewise phase correction technique, and/or other analytic techniques.

The identification component may be configured to identify the change(s) to the structure based on the analyses of the change in the signal characteristics of the received acoustic signal in time-domain, in frequency-domain, in mixed time-frequency-domain, and/or in other domains, and/or other information. In some implementations, identification of the change(s) to the structure based on the analyses of the change in the signal characteristics of the received acoustic signal in time-domain, in frequency-domain, and/or in mixed time-frequency-domain may include identification of the change(s) to the structure based on a combination of two or more results of the analyses of the change in the signal characteristics of the received acoustic signal in time-domain, in frequency-domain, and in mixed time-frequency-domain. The combination of the two or more results may include a weighted combination of the two or more results.

In some implementations, identification of the change(s) to the structure may include identification of one or more types and/or one or more causes of the change(s) to the structure. A type or a cause of the change(s) to the structure may include material loss, material conversion, material addition, and/or other material changes to the structure. The material loss may include pitting, cracking, fracturing of the structure, and/or other material loss of the structure. The material conversion may include corrosion of the structure and/or other material conversion of the structure. The material addition includes material migration, material accumulation, material adsorption, and/or other material addition to the structure.

In some implementations, identification of the type(s) and/or the cause(s) of the change(s) to the structure may include classification of the type(s) and/or the cause(s) of the change(s) to the structure. The classification of the type(s) and/or the cause(s) of the change(s) may be associated with a confidence level.

These and other objects, features, and characteristics of the system and/or method disclosed herein, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a," "an," and "the" include plural referents unless the context clearly dictates otherwise.

DETAILED DESCRIPTION

The present disclosure relates to combined analytic technique for differentiating changes to structures using acoustic signals. Combinations of multiple analytic techniques may be used to identify changes to a structure based on changes in characteristics of acoustic signals traveling along the structure. Acoustic signals traveling along the structure may be monitored to detect changes in characteristics of the acoustic signals from baseline signal characteristics. The changes in characteristics of the acoustic signals may be processed using multiple analytic techniques to provide analyses of the change in time-domain, in frequency-domain, and in mixed time-frequency-domain. The change (e.g., type of change, cause of change) to the structure may be identified based on a combination of the results of the analysis in time-domain, in frequency-domain, and in mixed time-frequency-domain.

Figure 1:
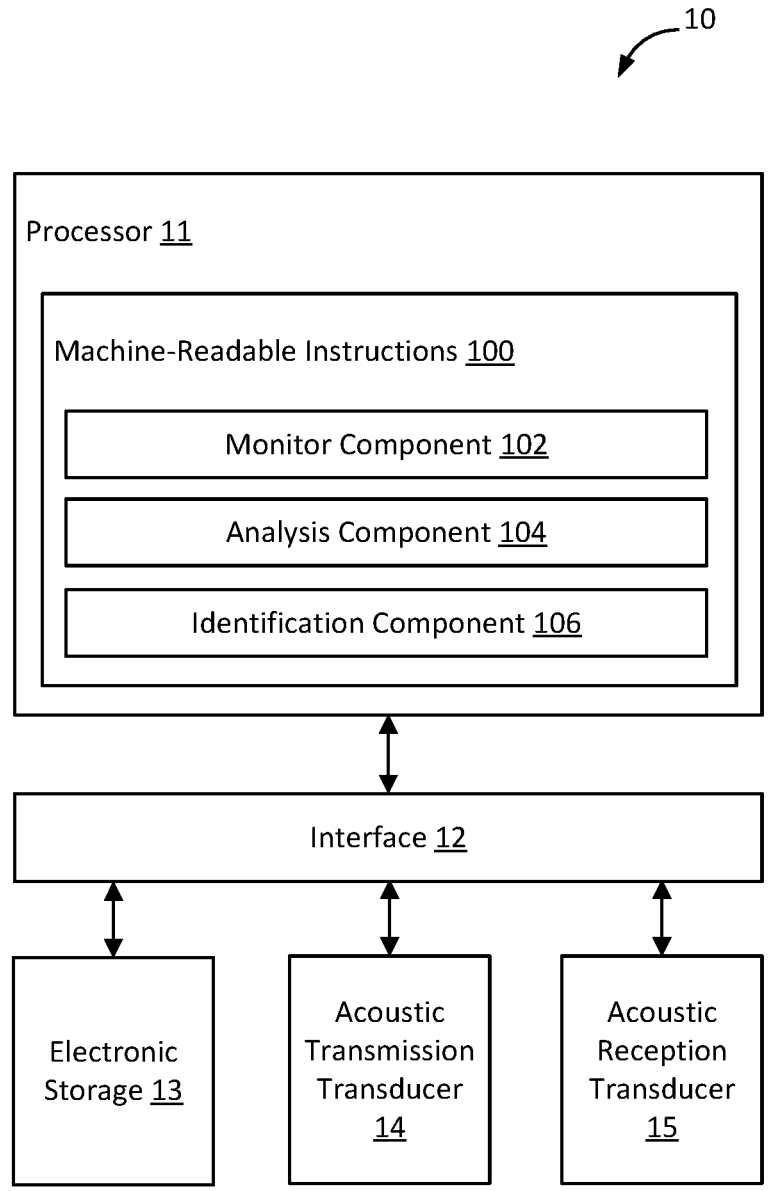
FIG. 1 illustrates an example system that identifies changes to a structure.

The methods and systems of the present disclosure may be implemented by and/or in a computing system, such as a system 10 shown in FIG. 1. The system 10 may include one or more of a processor 11, an interface 12 (e.g., bus, wireless interface), an electronic storage 13, an acoustic transmission transducer 14, an acoustic reception transducer 15, and/or other components.

The acoustic transmission transducer 14 may transmit one or more acoustic signals along a structure. The acoustic reception transducer 15 may receive the acoustic signal(s) after the acoustic signal(s) have traveled along at least a portion of the structure. The acoustic reception transducer 15 may generate output signals conveying signal characteristics of the received acoustic signal(s). The output signals may be monitored by the processor 11 for a change in the signal characteristics of the received acoustic signal(s) from baseline signal characteristics. The change in the signal characteristics of the received acoustic signal(s) may be caused by a change to the structure.

The change in the signal characteristics of the received acoustic signal(s) may be analyzed based on a set of analytic techniques and/or other information. The set of analytic techniques may provide analyses of the change in the signal characteristics of the received acoustic signal(s) in time-domain, in frequency-domain, in mixed time-frequency-domain, and/or other domains. The change to the structure may be identified based on the analyses of the change in the signal characteristics of the received acoustic signal(s) in time-domain, in frequency-domain, in mixed time-frequency-domain, and/or in other domains, and/or other information.

In some implementations, one or more components of the system 10 may be separate from the system 10. For example, the acoustic transmission transducer 14 may be separate from the system 10 and may be controlled by one or more processors separate from the processor 11. While the components of the system 10 are shown as single components, this is merely for example and is not meant to be limiting.

For example, while a single acoustic transmission transducer 14 and a single acoustic reception transducer 15 are shown in FIG. 1, the methods and systems of the present disclosure may include use of multiple acoustic transmission transducers placed along one or more portions of a structure and/or use of multiple acoustic reception transducers placed along one or more portions of the structure (e.g., along multiple points along the surface of the structure).

A structure may refer to arrangement and/or organization of one or more things. Thing(s) may be arranged and/or organized into a structure to perform one or more functions. A structure may be composed of a particular type of matter or a combination of different types of matter. Arrangement/organization of matter in the structure may allow one or more acoustic signals to travel along the structure. For example, a structure may include a metallic, rigid structure and/or other structure. A structure may have a symmetrical shape or an asymmetrical shape. A structure may include one or more simple geometric shapes, one or more arbitrarily complex geometric shapes, and/or other geometric shapes.

In some implementations, a structure may include one or more volumes (space) for holding, carrying, transporting, and/or otherwise interacting with one or more substances (e.g., particular kinds of matter) and/or one or more things. For example, a structure may include a pipe, a vessel, a container, a tank, and/or other structure. Such a structure may contain one or more fluids. A fluid may include water, oil, gas, chemical emulsion, and/or a mixture of different liquids, gases and/or solid particles. In some implementations, a structure may provide support for one or more substances and/or one or more things. For example, a structure may include a frame, a crane, a beam, a mechanical support, a flange, an elbow, a tee, a reducer, a weld, and/or other structure.

A change to a structure, such as material loss, material conversion, or material addition, may impact one or more functionalities of the structure. For example, a change to a pipe may impact the pipe's structural health, leading to deformation, fracture, or breakage. It may also impact the pipe's functionality to transport substance/thing through the pipe (e.g., reduce transport capacity). A change to a container may impact the container's functionality to hold/transport substance (e.g., increase possibility of container failure).

A change to a structure may result in a change to one or more signal characteristics of acoustic signals traveling along the structure. For example, small mechanical or physical changes in the structure may lead to scattering and/or attenuation of broadband acoustic signals, which may be detectable as changes in signal characteristics of the acoustic signals. The change to the signal characteristic(s) of the acoustic signal may be analyzed to identify the change to the structure. Analyses of the change to the signal characteristic(s) of the acoustic signal may include analyses of the change in time-domain, in frequency-domain, and in mixed time-frequency-domain to differentiate between different changes and/or different sources of changes to the structure.

Analyses in the different domains may be used to predict with confidence what change in the structure (e.g., material loss) caused the change in the acoustic signal characteristics(s) (e.g., measured acoustic response). For example, mechanical perturbations of the structure that lead to acoustic scattering and attenuation may be be due to material loss (pitting, cracks, fractures), material conversion (corrosion products), and/or material addition (material migration and accumulation, material adsorption), each of which may have particular scattering/attenuation characteristics in the amplitude-time-frequency phase space. The time-domain, frequency-domain, and in mixed time-frequency-domain analyses may be used to distinguish between different sources of change(s) to the signal characteristic(s), such as corrosion versus accumulated water on pipe walls. For instance, signal characteristics of an acoustic signal traveling along a pipe may change as a function of pipe characteristics, such as type and condition of coating on the pipe. Different types and conditions of coating of pipe may lead to different frequency-dependent attenuation effects on the acoustic signal transmission. Analysis of the change in the signal characteristics of the received acoustic signal may be used to identify the type, thickness, and/or the condition of the coating on the pipe.

The acoustic transmission transducer 14 may refer to a device configured to convert energy from one form to another. The acoustic transmission transducer 14 may be configured to convert a signal in one form of energy to a signal in another form of energy. The acoustic transmission transducer 14 may be configured to convert a received signal into one or more acoustic signals. The acoustic transmission transducer 14 may be configured to generate the acoustic signal(s) for transmission along a structure. The acoustic transmission transducer 14 may be configured to transmit the acoustic signal(s) along a structure, such as from one part of the structure to another part of structure, or from one end of the structure to another end of the structure.

An acoustic signal transmitted by the acoustic transmission transducer 14 may have one or more certain (chosen) amplitude time-frequencies to excite multiple modes of acoustic propagation in the structure. For example, one or more amplitude-time frequency characteristics of an acoustic signal may be tuned for one or more structures and/or one or more changes to the structure. Specific amplitude-time-frequency characteristic(s) may be used for specific structure (e.g., acoustic signals with different amplitude-time-frequency characteristics are transmitted for pipe versus tank). Specific amplitude-time-frequency characteristic(s) may be used for specific change to structure (e.g., acoustic signals with different amplitude-time-frequency characteristics are transmitted to detect different changes to the structure).

In some implementations, acoustic signals with different amplitude-time-frequency characteristics may be generated by different hardware. For example, different hardware/combinations of hardware may be used to generate acoustic signals with different amplitude-time-frequency characteristics. For instance, specific hardware may be used to generate acoustic signals that are optimized for a specific type of structure (e.g., pipe, vessel, tank) and/or an anticipated change (e.g., anticipated defect in the structure).

The acoustic reception transducer 15 may refer to a device configured to convert energy from one form to another. The acoustic reception transducer 15 may be configured to convert a signal in one form of energy to a signal in another form of energy. The acoustic reception transducer 15 may be configured to convert a received acoustic signal into one or more output signals. The acoustic reception transducer 15 may be configured to receive one or more acoustic signals transmitted by the acoustic transmission transducer 14 after the acoustic signal(s) have traveled along at least a portion of the structure. The acoustic reception transducer 15 may be configured to generate output signals conveying signal characteristics of the received acoustic signal(s) and/or other information. The acoustic data acquisition (e.g., acoustic signal reception, output signal generation) may be configured for high signal-to-noise ratio in the probed structure.

The acoustic transmission transducer 14 and the acoustic reception transducer 15 may be used to transmit acoustic signal(s) along a structure and receive the transmitted acoustic signal(s) at different times. The signals transmitted/received at different times may be used to determine changes to the characteristic(s) of the acoustic signal(s). For example, an initial acoustic signal transmission/reception may be used to establish baseline signal characteristics of an acoustic signal traveling along a structure. The baseline signal characteristics may reflect the initial (baseline) condition of the structure. The baseline signal characteristics may reflect the condition of the structure from which changes are to be identified. Subsequent acoustic signal transmission/reception may be used to determine changes in the signal characteristics of the acoustic signal. A change in the signal characteristics of the acoustic signal may include a change between the signal characteristics of the subsequent acoustic signal and the baseline signal characteristics (signal characteristics of the initial/baseline acoustic signal). The change in the signal characteristics of the acoustic signal may be analyzed in different domains to identify the change to the structure.

Figure 3:
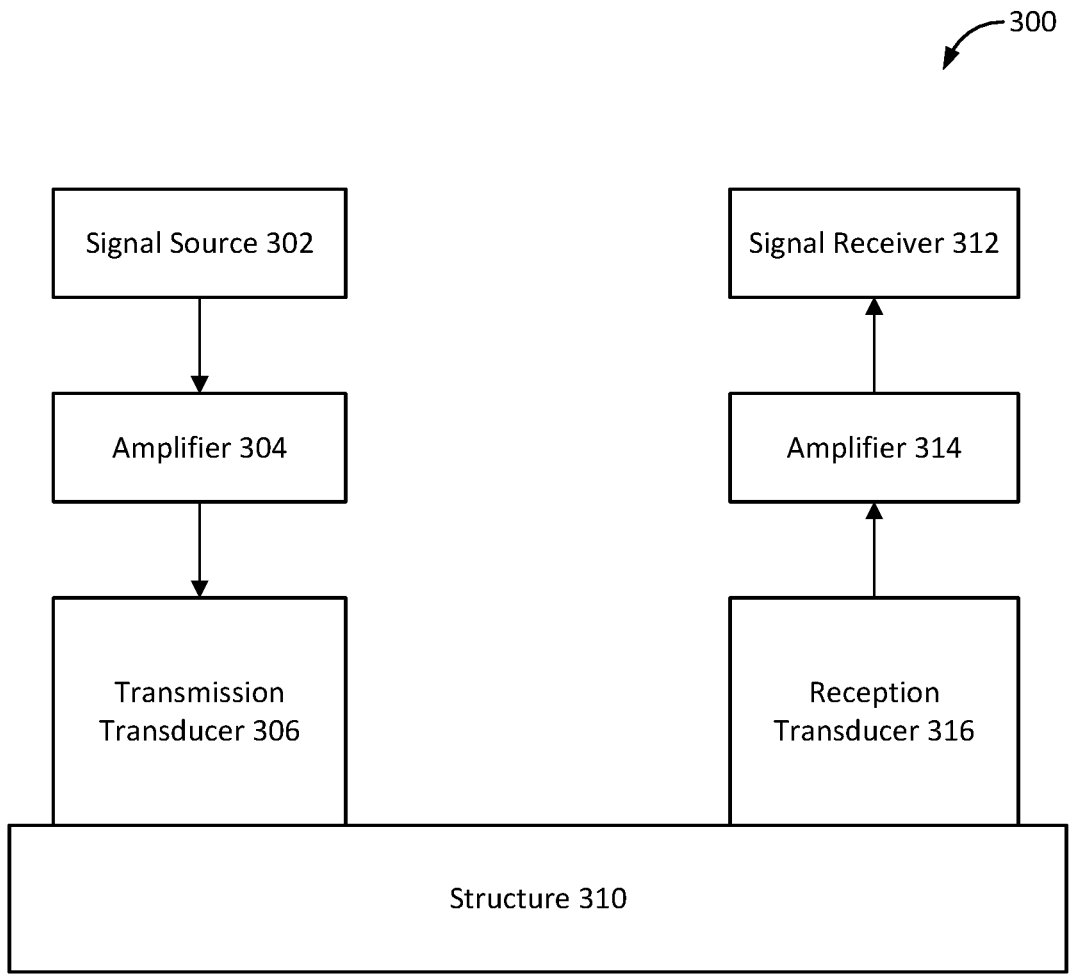
FIG. 3 illustrates an example use of acoustic signal for identifying changes to a structure.

FIG. 3 illustrates an example use of acoustic signal for identifying changes to a structure 310. A signal source 302 may provide an acoustic signal with one or more chosen signal characteristics. The acoustic signal may be amplified by an amplifier 304, and passed onto a transmission transducer 306. The transmission transducer 306 and a reception transducer 316 may be coupled to the structure 310. Coupling between the structure 310 and the transducers 306, 316 may include embedding, mechanical attachment, non-contact air coupling, remote light coupling, and/or other coupling. The transmission transducer 306 may transmit acoustic signal(s) along the structure 310. The acoustic signal(s) may be single mode, multimode, broadband, narrowband, and/or other types of signals. The acoustic signal(s) may be detected by the reception transducer 316 after the acoustic signal(s) have traveled along at least a portion of the structure 310. The reception transducer 316 may convert the received acoustic signal into output (electrical) signals. The output signals may be amplified by an amplifier 314 before being passed onto a signal receiver 312. The acoustic signal from the signal source 302 and/or the received acoustic signal may be synchronized and processed by the signal receiver 312. In some implementations, one or more of the signal source 302, the amplifier 304, and/or the transmission transducer 306 may be included within the acoustic transmission transducer 14. In some implementations, one or more of the signal receiver 312, the amplifier 314, and/or the reception transducer 316 may be included within the acoustic reception transducer 15.

In some implementations, multiple transmission transducers and multiple reception transducers may be coupled to the structure 310. Portions of the structure 310 between individual transmission-reception-transducer pairs may form inspection zones. Changes in signal characteristics of acoustic signal that travel through individual inspection zones may be used to identify one or more changes to the structure 310 within individual inspection zones and may enable monitoring of the structure 310 in segments. Such detection of changes to the structure 310 may allow for localization of changes within the structure 310. In some implementations, transmission-reception-transducer pairs may be coupled to the structure 310 such that individual segments are of uniform size.

In some implementations, transmission transducers and reception transducers may be placed along a structure to account for irregular shape of the structure. For instance, for portions/segments of the structure with irregular geometric shapes, multiple/additional transmission transducers and/or multiple/additional reception transducers may be used to transmit and receive acoustic signal(s). Increase in number of transmission transducers may facilitate more uniform acoustic excitation of the structure and lead to better sensitivity, selectivity, and/or robustness of the structural change detection based on acoustic signals. Increase in number of reception transducers may increase redundancy of the system, which may increase the reliability and robustness of the structural change detection based on acoustic signals.

Referring back to FIG. 1, the electronic storage 13 may be configured to include electronic storage medium that electronically stores information. The electronic storage 13 may store software algorithms, information determined by the processor 11, information received remotely, and/or other information that enables the system 10 to function properly. For example, the electronic storage 13 may store information relating to acoustic signals, information relating to transmission of acoustic signals, information relating to reception of acoustic signals, information relating to output signals, information relating to signal characteristics, information relating to changes in signal characteristics, information relating to baseline signal characteristics, information relating to structures, information relating to changes to structures, information relating to analytic techniques, information relating to analyses of change in signal characteristics in time-domain, in frequency-domain, and/or in mixed time-frequency-domain, information relating to identification of changes to structures, and/or other information.

The processor 11 may be configured to provide information processing capabilities in the system 10. As such, the processor 11 may comprise one or more of a digital processor, an analog processor, a digital circuit designed to process information, a central processing unit, a graphics processing unit, a microcontroller, an analog circuit designed to process information, a state machine, and/or other mechanisms for electronically processing information. The processor 11 may be configured to execute one or more machine-readable instructions 100 to facilitate identifying changes to a structure using acoustic signals. The machine-readable instructions 100 may include one or more computer program components. The machine-readable instructions 100 may include one or more of a monitor component 102, an analysis component 104, an identification component 106, and/or other computer program components.

The monitor component 102 may be configured to monitor the output signals conveying signal characteristics of the received acoustic signal for a change in the signal characteristics of the received acoustic signal. The change in the signal characteristics of the received acoustic signal may be caused by one or more changes to the structure. Monitoring the output signals may include one or more of checking, examining, tracking, observing, watching, and/or otherwise monitoring the output signals. The monitor component 102 may monitor the output signals continuously, periodically, on-demand, and/or based on other basis. For example, the monitor component 102 may monitor the output signals as the output signals are received/generated. The monitor component 102 may monitor the output signals at a periodic rate (e.g., a set number of times per day/week/month/year). The monitor component 102 may monitor the output signals based on user/system command to monitor the output signals. Other basis for monitoring the output signals are contemplated.

The monitor component 102 may monitor the output signals to determine whether there is any change or a particular change in the signal characteristics of the received acoustic signal. For example, the monitor component 102 may monitor the output signals to determine whether one or more of the signal characteristics has changed at all and/or has changed beyond a certain amount (e.g., beyond threshold amount).

A signal characteristic of an acoustic signal may refer to a feature and/or a quality of the acoustic signal. A signal characteristic of an acoustic signal may relate to one or more of amplitude, wavelength, period, frequency and/or other features/qualities of the acoustic signal. A signal characteristic of an acoustic signal may include a time-varying characteristic, a frequency-varying characteristic, and/or other varying characteristics.

A signal characteristic of an acoustic signal may include a static characteristic (e.g., a characteristic that does not change with respect to time and/or frequency) or a dynamic characteristic (e.g., a characteristic that changes with respect to time and/or frequency). For example, the monitor component 102 may monitor the output signals to determine a change in one or more amplitude-time frequency characteristics (amplitude characteristic, time characteristic, frequency characteristic) of the received acoustic signal, which may have been caused by one or more changes to the structure.

A change in the signal characteristics of the received acoustic signal may include a change between one or more of the signal characteristics of the received acoustic signal from one or more of baseline signal characteristics. A change in the signal characteristics of the received acoustic signal may include one or more differences between the signal characteristics of the received acoustic signal and the baseline signal characteristics. Other changes in the signal characteristics of the received acoustic signal are contemplated.

Monitoring the output signals conveying signal characteristics of the received acoustic signal for a change in the signal characteristics of the received acoustic signal may include determining a difference between the received acoustic signal/signal characteristics and a baseline signal/baseline signal characteristics. For example, differential signal changes may be determined by taking a difference between a previously recorded baseline signal and the received acoustic signal. Differential signal characteristic changes may be determined by taking a difference between a previously recorded baseline signal characteristics and the signal characteristics of the received acoustic signal.

Baseline signal characteristics may refer to characteristics to be used for comparison. Baseline signal characteristics may refer to signal characteristics of a baseline signal transmitted through the structure. A baseline signal may refer to an acoustic signal transmitted through the structure when the structure is in a known state/condition and/or baseline state/condition. For example, an initial acoustic signal transmission/reception may be used to establish baseline signal characteristics of an acoustic signal traveling along a structure. The baseline signal characteristics may characterize the state/condition of the structure when the initial acoustic signal was transmitted/received through the structure.

For instance, the initial acoustic signal may be transmitted/received through the structure when the structure is installed and/or after a detailed inspection in which the condition of the structure is determined. Once the structure is characterized in a known state/condition by the baseline signal characteristics, signal characteristics of subsequent acoustic signals that are transmitted/received through the structure may be monitored to detect deviations from the baseline signal characteristics. Deviation of the signal characteristics from the baseline signal characteristics may indicate that the structure has changed (e.g., defect formation) compared to when the baseline signal characteristics was established.

The analysis component 104 may be configured to analyze the change in the signal characteristics of the received acoustic signal based on a set of analytic techniques and/or other information. Analysis of a change in the signal characteristics may include one or more of examination, investigation, breakdown, processing, and/or other analysis of the change in the signal characteristics. The analysis component 104 may analyze the change in the signal characteristics of the received acoustic signal responsive to reception of the acoustic signal and/or responsive to detection of the change in the signal characteristics. The analysis component 104 may analyze the change in the signal characteristics of the received acoustic signal responsive to detection of any change in the signal characteristics and/or a particular change (e.g., change beyond a threshold amount) in the signal characteristics. The analysis component 104 may analyze the change in the signal characteristics of the received acoustic signal continuously, periodically, on-demand, and/or based on other basis.

The set of analytic techniques may provide analyses of the change in the signal characteristics of the received acoustic signal in time-domain, in frequency-domain, in mixed time-frequency-domain, and/or in other domains. For example, the set of analytic techniques may provide analyses of the difference between the amplitude-time frequency characteristics of the received acoustic signal from the baseline signal characteristics in time-domain, in frequency-domain, in mixed time-frequency-domain, and/or in other domains. Other analysis of the change in the signal characteristics of the received acoustic signal are contemplated.

The set of analytic techniques may include one or multiples (e.g., two or more) of a short-time-Fourier-transform difference maximum technique, a time-integrated mean technique, a time-integrated standard deviation technique, an auto-correlation mean technique, an auto-correlation standard deviation technique, a time-shift mean technique, a time-shift standard deviation technique, a piecewise phase correction technique, and/or other analytic techniques. Individual techniques may be used to identify one or more certain features in the received acoustic signal. Analysis in time-domain, in frequency-domain, in mixed time-frequency-domain, and/or in other domains provided by the set of analytic techniques may enable differentiation of different changes to the structure. For example, analysis in time-domain, in frequency-domain, in mixed time-frequency-domain, and/or in other domains may enable differentiation of types and/or causes of changes to the structure.

Relationships between different perturbation characteristics and different analytic techniques may be established. For example, different analytic techniques may be applied to a variety of controlled perturbation effects on different structures to establish the relationships between different changes to the structures and different results of the analytic techniques. The relationships may be stored (e.g., in a database, a library) and used to map measured signal characteristics and/or analytic technique results for structural change identification (e.g., defect identification). The analytic methods may show significant perturbation-dependent sensitivity and may be used in combination to predict with confidence what change in the structure (e.g., perturbation effect) caused the change in the acoustic signal characteristics(s) (e.g., measured acoustic response).

The short-time-Fourier-transform difference maximum technique (STFTdiffMax) may provide analysis of the change in the signal characteristics of the received acoustic signal in the mixed time-frequency-domain. The short-time-Fourier-transform difference maximum technique may include application of short-time-Fourier-transform on one or more of the received acoustic signal, the signal characteristics of the received acoustic signal, the differential signal change (difference between the received acoustic signal and the baseline signal), and/or the differential signal characteristic change (difference between the signal characteristics of the received acoustic signal from the baseline signal characteristics) to generate a map. In some implementations, the parameters of the short-time-Fourier-transform (e.g., window size, step size) may depend on the structure (e.g., structure dimensions, structure characteristics).

The map may include a frequency axis and a time axis, and may characterize signal intensities as a function of frequency and time. The map may define the distribution of received signal strength as a function of time and frequency. The map may define at which frequency, when, and with what strength the signal arrived. The map may include one or more time-frequency pairs that show large differences between signal characteristics. The change to the structure may be identified based on the largest difference in the map. The short-time-Fourier-transform difference maximum technique may provide overall quantitative estimate for the change to the structure.

The map may include a STFT difference map. The STFT difference map define the difference in signal intensities of the received acoustic signal and the baseline signal. The STFT difference map may be generated based on the differential signal change and/or the differential signal characteristic change. The STFT difference map may be generated as a difference between the STFT map of the received acoustic signal and the STFT map of the baseline signal. The baseline STFT map may define a reference level against which perturbation effects/structural change may be analyzed.

The time-integrated mean technique (TimeIntegMean) may provide analysis of the change in the signal characteristics of the received acoustic signal in the frequency-domain. The time-integrated mean technique may use the map generated from the short-time-Fourier-transform difference maximum technique and/or other information. The time-integrated mean technique may include integration of the map (e.g., STFT difference map) in the time domain to reduce the information contained within the into a lower dimensional information (e.g., curve) in the frequency domain. By integrating overtime, the time-dependence in the analyzed signal may be averaged out. The lower dimensional information may be used to identify features with certain (e.g., prominent) frequency components. The time-integrated mean technique may determine the mean of the lower dimensional information. Integration of the map in the frequency domain, rather than the time domain, may be used in frequency-integrated mean technique.

The time-integrated standard deviation technique (TimeIntegStd) may provide analysis of the change in the signal characteristics of the received acoustic signal in the frequency-domain. The time-integrated standard deviation technique may use the lower dimensional information generated from the time-integrated mean technique, generation of the lower dimensional information as discussed with respect to the time-integrated mean technique, and/or other information. The time-integrated standard deviation technique may include analysis of the lower dimensional information in the frequency domain to determine the standard deviation (e.g., deviation of the mean). The measure of the standard deviation may provide information on how much scattering occurred within the domain and how the scattering is distributed in the frequency domain. Integration of the map in the frequency domain, rather than the time domain, may be used in frequency-integrated standard deviation technique.

The auto-correlation mean technique (AutoCorrMean) may provide analysis of the change in the signal characteristics of the received acoustic signal in the mixed time-frequency-domain. The auto-correlation mean technique may use the map generated from the short-time-Fourier-transform difference maximum technique and/or other information. The auto-correlation mean technique may include application of an auto correlation function on the map (e.g., STFT difference map), which may provide information on whether repetitive patterns exist in the mixed frequency-time-domain. The auto-correlation mean technique may determine the mean of the auto-correlated information. The results of the auto-correlation mean technique may provide information on occurrence of one or more scattering events that led to loss of or increase in energy at specific time and frequency. The results of the auto-correlation mean technique may be used to identify (large) changes in the structure that lead to (large) scattering in the received acoustic signal.

The auto-correlation standard deviation technique (AutoCorrStd) may provide analysis of the change in the signal characteristics of the received acoustic signal in the mixed time-frequency-domain. The auto-correlation standard deviation technique may use the map generated from the short-time-Fourier-transform difference maximum technique and/or other information. The auto-correlation standard deviation technique may include application of an auto correlation function on the map (e.g., STFT difference map). The auto-correlation mean technique may determine the standard deviation of the auto-correlated information. The standard deviation of the signal as a function of time and frequency may provide information on the number of scattering events in the structure/portion of the structure under investigation. Larger standard deviation values may be indicative of larger number of scattering events in the structure and smaller standard deviation values may be indicative of smaller number of scattering events in the structure.

The time-shift mean technique (TimeShiftMean) may provide analysis of the change in the signal characteristics of the received acoustic signal in the time-domain. The time-shift mean technique may include determination of the phase difference of fast Fourier transform of the received acoustic signal and the baseline signal or the difference signal (difference between the received acoustic signal and the baseline signal) and determination of the mean divided by the total phase. The results of the time-shift mean technique may used to determine a change to the structure based on delay information. Based on the delay information (time delay), certain characteristics of the change in the structure may be determined. For example, based on the mode and group velocity, the time delay may be indicative of what type of scattering effect may have occurred in the structure.

The time-shift standard deviation technique (TimeShiftStd) may provide analysis of the change in the signal characteristics of the received acoustic signal in the time-domain. The time-shift standard deviation technique may include determination of the phase difference of fast Fourier transform of the received acoustic signal and the baseline signal or the difference signal and determination of the standard deviation divided by the total phase. The results of the time-shift standard deviation technique may be used to determine a change to the structure based on delay information (time delay). Based on the delay information, the number of scattering events and/or the distribution of the scattering events in time may be determined in terms of their delay.

The piecewise phase correction technique (PPhaseC) may provide analysis of the change in the signal characteristics of the received acoustic signal in the time-domain. The piecewise phase correction technique may include application of a piecewise phase correction function to identify changes in the structures. For example, based on the phase shift, the types of changes to the structure may be identified. For instance, larger phase shift may be indicative of inelastic scattering, larger energy absorption, remission at different phase, and/or other change to the structure, while smaller phase shift and/or no phase shift may be indicative of elastic scattering and/or other change to the structure.

In some implementations, one or more temperature compensation techniques may be applied to the analyses of the change in the signal characteristics of the received acoustic signal. Temperature changes in and/or around the structure may affect the behavior of the acoustic signal traveling along the structure. Thus, changes in environmental and/or operational conditions of the structure may change the signal characteristics of the receive acoustic signal and introduce noise in the analysis. A temperature compensation technique may include (1) ultrasonic excitation with multiple modes, or hybridized modes, in specular and diffuse regimes; (2) ultrasonic propagation in homogeneous and non-homogenous media involving multiple reflections, and broad spectral and wide temporal range signals; and (3) autonomous compensation with a wide range of global and local temperature fluctuations in the interrogated medium without the need to know the actual global or local temperatures. The temperature compensation technique may correct spurious temperature effects while not significantly altering the actionable signal due to changes to the structure. Other temperature compensation techniques are contemplated.

The identification component 106 may be configured to identify the change(s) to the structure based on the analyses of the change in the signal characteristics of the received acoustic signal in time-domain, in frequency-domain, in mixed time-frequency-domain, and/or in other domains, and/or other information. Analysis in time-domain, in frequency-domain, in mixed time-frequency-domain, and/or in other domains may enable differentiation of different changes to the structure. The results of the analysis in the time-domain, in frequency-domain, in mixed time-frequency-domain, and/or in other domain may be used to identify the change(s) to the structure based on relationships between different changes to the structure and the corresponding (expected, calculated, previously determined) results of the analysis in the time-domain, in frequency-domain, in mixed time-frequency-domain, and/or in other domains.

The identification component 106 may match the results of the analyses of the change in the signal characteristics of the received acoustic signal in time-domain, in frequency-domain, in mixed time-frequency-domain, and/or in other domains with the result-change relationships (e.g., stored in a database, stored in a library) and map the measured signal characteristics and/or analytic technique results for structural change identification (e.g., defect identification).

In some implementations, identification of the change(s) to the structure may include identification of one or more types and/or one or more causes of the change(s) to the structure. A type of changes to the structure may refer to a category of changes to the structure. A cause of the changes to the structure may refer to a source of the changes to the structure. For example, a type and/or a cause of the changes to the structure may include material loss, material conversion, material addition, and/or other material changes to the structure. The material loss may include pitting, cracking, fracturing of the structure, and/or other material loss of the structure. The material conversion may include corrosion of the structure and/or other material conversion of the structure. The material addition includes material migration, material accumulation, material adsorption, and/or other material addition to the structure. Other changes to the structure are contemplated. In some implementations, identification of the change(s) to the structure may include quantification of the change(s) to the structure. Quantification of a change to the structure may refer to measurement of the change to the structure. The change to the structure may be quantified in terms of numbers, percentages, levels, and/or other quantitative terms.

In some implementations, identification of a type and/or a cause of a change to the structure may include classification of the type and/or the cause of the change to the structure. Classification of the type and/or cause of the change to the structure may include categorization and/or grouping the type and/or the cause based on shared qualities and/or characteristics. A classification of the type and/or the cause of the change may be associated with a confidence level. The confidence level may indicate the accuracy level of the classification. The confidence level may indicate the extent of confidence (e.g., high, low, percentage value) with which the measured acoustic response was caused by the identified change to the structure.

In some implementations, identification of the change(s) to the structure based on the analyses of the change in the signal characteristics of the received acoustic signal in time-domain, in frequency-domain, in mixed time-frequency-domain, and/or in other domain may include identification of the change(s) to the structure based on a combination of two or more results of the analyses of the change in the signal characteristics of the received acoustic signal in time-domain, in frequency-domain, in mixed time-frequency-domain, and/or in other domain. For instance, individual results of the analysis in the time-domain, in frequency-domain, and/or in mixed time-frequency-domain may not be deterministic and may be insufficient to identify the change (e.g., type of defect) to the structure. The combination of two or more of the results of the analysis in the time-domain, in frequency-domain, and/or in mixed time-frequency-domain may be used to determine probabilities of different changes to the structure causing the change in the signal characteristics of the received acoustic signal. Database/library of different changes to the structure and different results of analyses (e.g., artificially produced, field tested, interpolated) may be used to correlate different changes to the signal characteristics of the received acoustic signal with different changes to the structure.

The combination of two or more of the results of the analysis in the time-domain, in frequency-domain, in mixed time-frequency-domain, and/or other domain may include joining or merging of the results. For example, two or more of the results may be combined additively, multiplicatively, and/or through other combinations. The combination of two or more results may include a weighted combination of the two or more results. That is, the change to the structure may be determined based on weighting of the results of the different analytic methods. Weighting of the results of the different analytic methods may be based on the individual analytical methods, the structure being investigated, the change being investigated, and/or other information. Weighting of the results may enable identification of changes to the structure with no undercall and no overcall. Weighting of the results may improve the reliability of the change identified (predicted) based on the change in the signal characteristics of the received acoustic signal.

Figure 4:
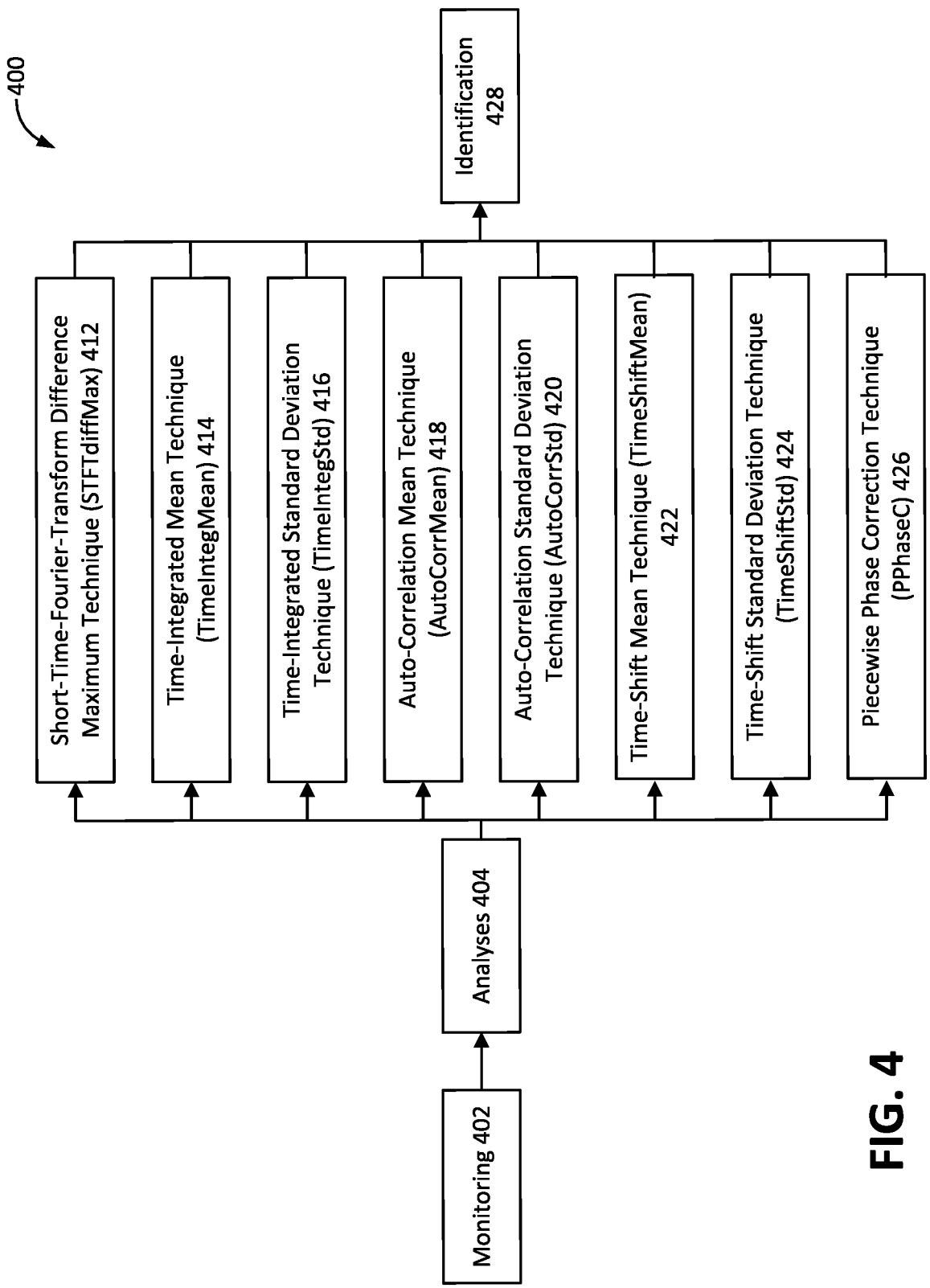
FIG. 4 illustrates an example flow diagram for identifying changes to a structure.

FIG. 4 illustrates an example flow diagram 400 for identifying changes to a structure. The flow diagram 400 may include a monitoring step 402, where signal characteristics of an acoustic signal that traveled along a structure is monitored to detect a change in the signal characteristics of the acoustic signal. The change in the signal characteristics of the acoustic signal may include a difference between the signal characteristics of the acoustic signal from baseline signal characteristics.

The flow diagram 400 may proceed to an analyses step 404. The analyses step 404 may include analyses of the change in the signal characteristics of the received acoustic signal in time-domain, in frequency-domain, and in mixed time-frequency-domain. The analyses in the different domains may be provided by a set of analytic techniques. The set of analytic techniques may include a short-time-Fourier-transform difference maximum technique 412, a time-integrated mean technique 414, a time-integrated standard deviation technique 416, an auto-correlation mean technique 418, an auto-correlation standard deviation technique 420, a time-shift mean technique 422, a time-shift standard deviation technique 424, a piecewise phase correction technique 426, and/or other analytic techniques. While different analytic techniques are shown as proceeding in parallel in FIG. 4, this is merely for ease of reference and is not meant to be limiting. In some implementations, two or more of the analytic techniques may be performed in sequence (one after another). In some implementations, one or more of the analytic techniques may utilize information from one or more other analytic techniques.

The flow diagram 400 may proceed to an identification step 428. The identification step 428 may include identification of a change to the structure based on the analyses of the change in the signal characteristics of the received acoustic signal in time-domain, in frequency-domain, and in mixed time-frequency-domain. The identification step 428 may use a weighted combination of two or more results from the short-time-Fourier-transform difference maximum technique 412, the time-integrated mean technique 414, the time-integrated standard deviation technique 416, the auto-correlation mean technique 418, the n auto-correlation standard deviation technique 420, the time-shift mean technique 422, the time-shift standard deviation technique 424, the piecewise phase correction technique 426, and/or other analytic techniques to identify the change to the structure.

Figure 5:
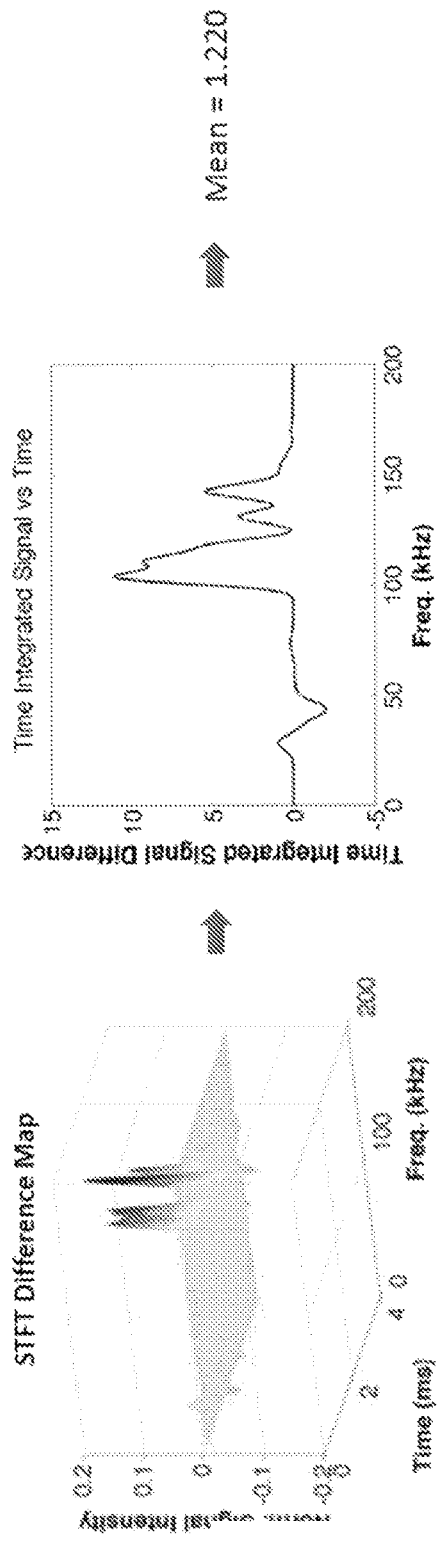
FIG. 5 illustrates example analyses using time-integrated mean technique and time-integrated standard deviation technique.
Figure 5:
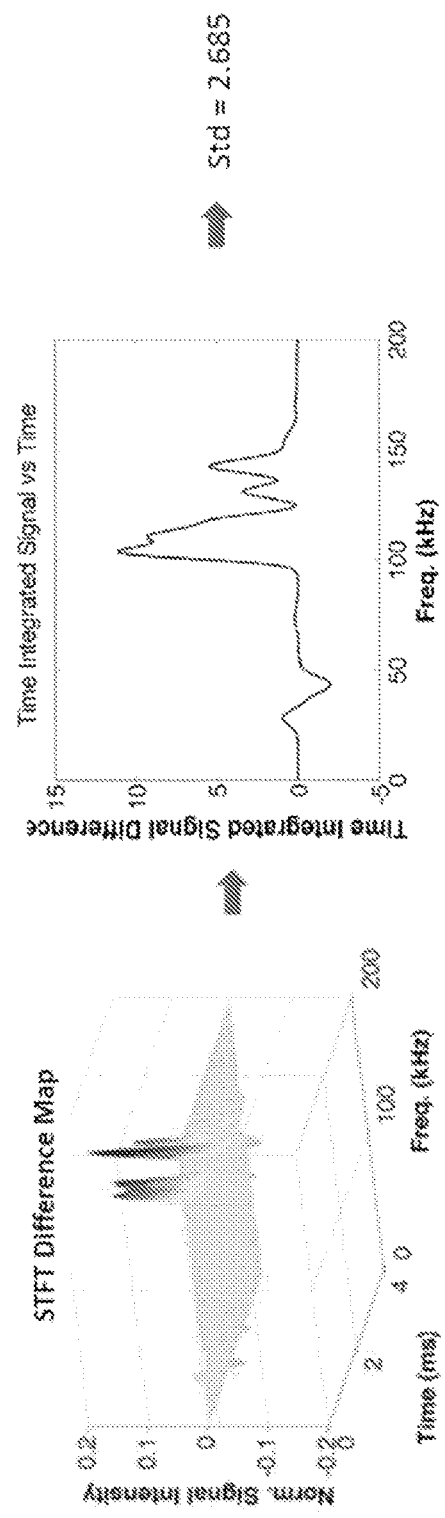

FIG. 5 illustrates example analyses using time-integrated mean technique and time-integrated standard deviation technique. The time-integrated mean technique and the time-integrated standard deviation technique may include integration of a STFT difference map over time. The STFT difference map may include a three-dimensional plot/contour map. The STFT difference map may define magnitude of signal at specific points in the time-frequency space. A time integrated signal vs time curve may be obtained by integrating the STFT difference map over time. The time integrated signal vs time curve may show changes in signal difference as a function of frequency.

In the time-integrated mean technique, the time integrated signal vs time curve may be used to calculate the mean of the signal. The mean of the curve may reflect and/or be indicative of the strength of the signal, which may be used for analysis in identification of the change to the structure. In the time-integrated standard deviation technique, the time integrated signal vs time curve may be used to calculate the standard deviation of the signal. The time-integrated standard deviation technique may provide information of difference of each point on the curve from the mean and provide a measure in terms of standard deviation.

Figure 6:
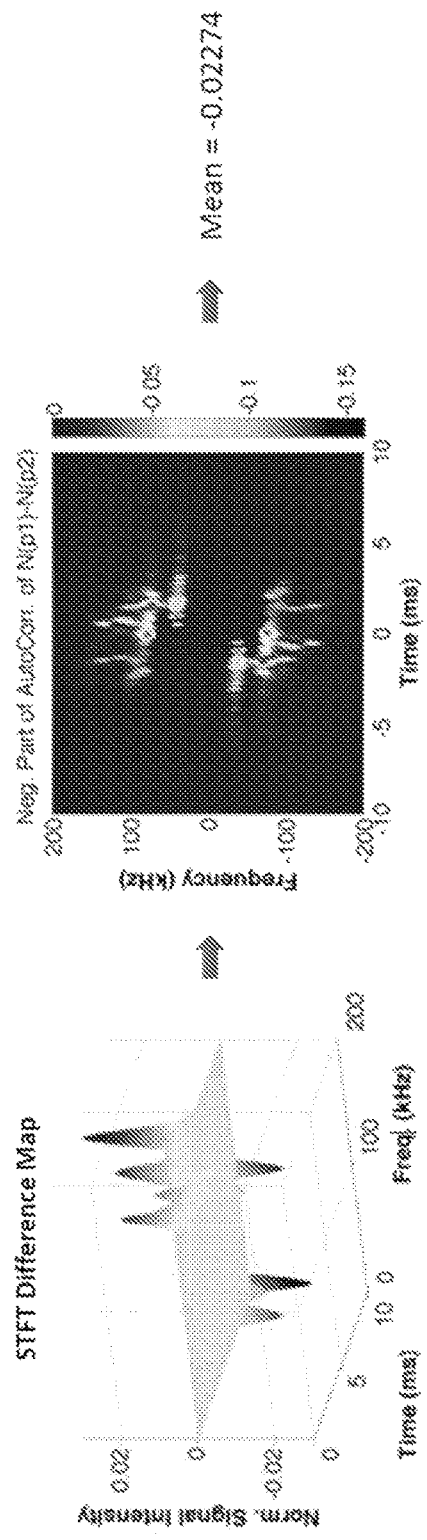
FIG. 6 illustrates example analyses using auto-correlation mean technique and auto-correlation standard deviation technique.
Figure 6:
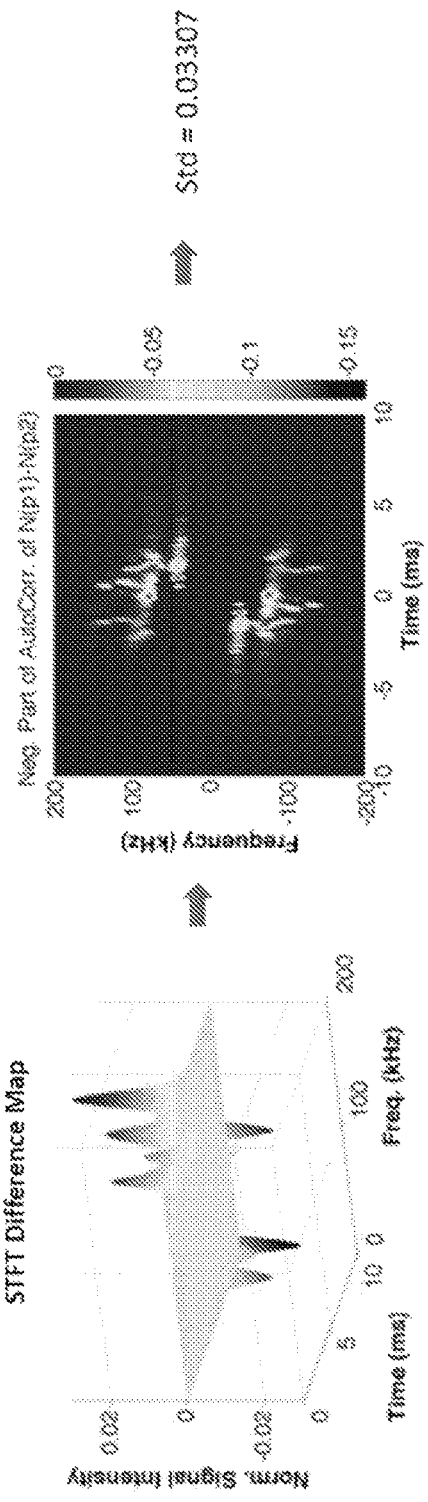

FIG. 6 illustrates example analyses using auto-correlation mean technique and auto-correlation standard deviation technique. The auto-correlation mean technique and the auto-correlation standard deviation technique may include auto correlation of the data within the STFT difference map to highlight ups and downs in the STFT difference map. Specific pairs of activity in the auto-correlated map may be used to identify change to the structure. For example, pairs of large activity in the auto-correlated map may be used to identify scattering events. One specific time-frequency attribute may be matched to another one of the opposite sign, which may correspond to a scattering where, at a certain frequency and time, energy was lost or increased. The change in energy may be used to identify (strong) scattering events within the structure. In the auto-correlation mean technique, the negative peak values of the auto-correlated map may be used to identify scattering events that lead to loss of energy in one acoustic mode and gain of energy in another acoustic mode. In the auto-correlation standard deviation technique, the negative values of the auto-correlated map may be used to calculate the standard deviation of such scattering events.

Figure 7:
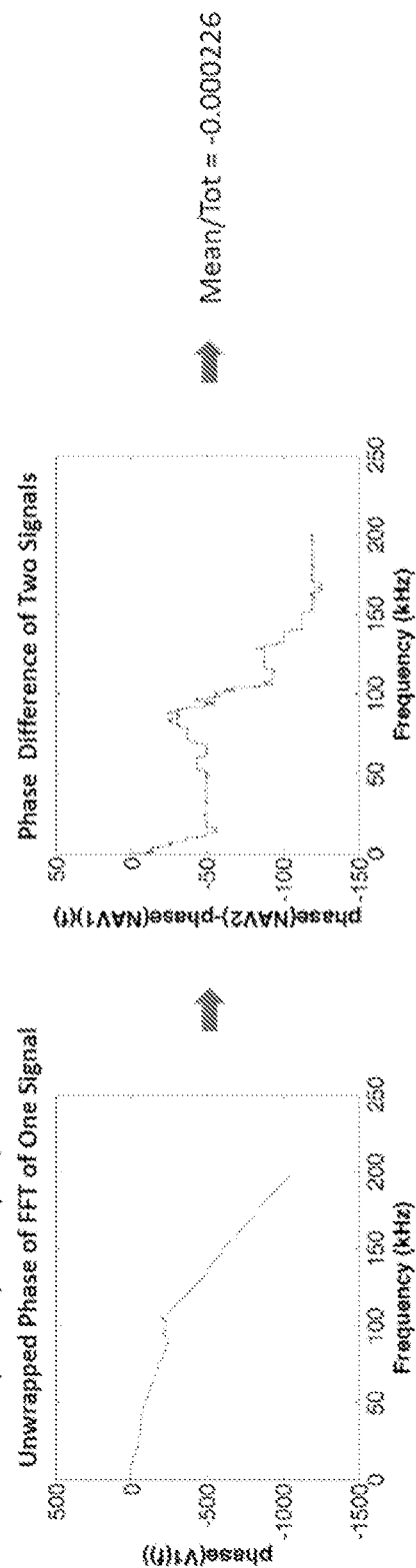
FIG. 7 illustrates example analyses using time-shift mean technique and time-shift standard deviation technique.
Figure 7:
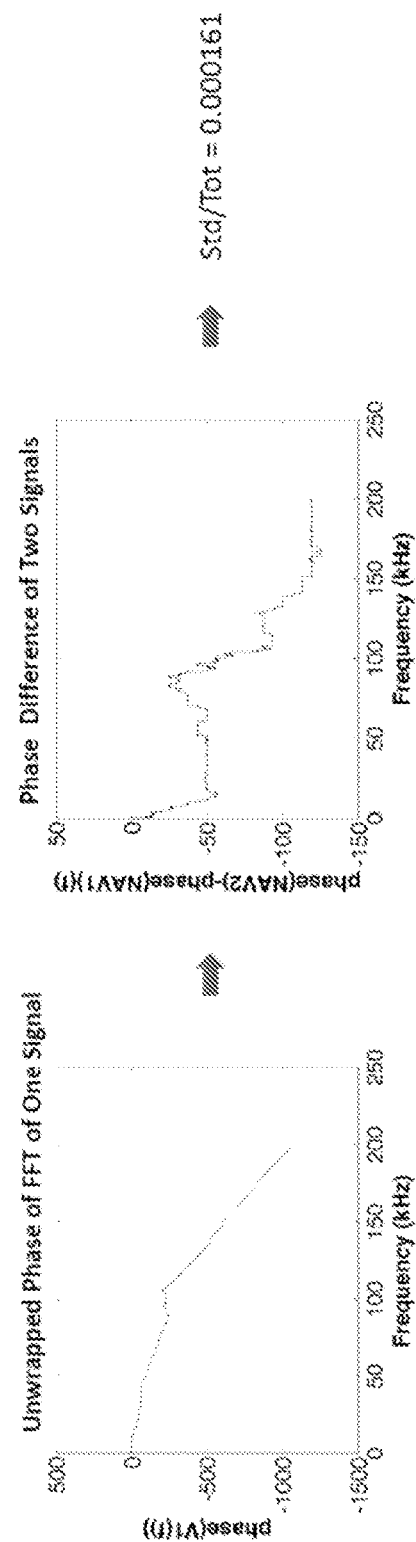

FIG. 7 illustrates example analyses using time-shift mean technique and time-shift standard deviation technique. The time-shift mean technique and time-shift standard deviation technique may include fast Fourier transform of the difference signal (e.g., difference between a baseline signal and a received acoustic signal) to obtain both phase and spectral information about the difference signal. In the time-shift mean technique, phase difference of the baseline signal and the received acoustic signal may be used to determine the mean, which may be normalized with respect to the total phase. In the time-shift standard deviation technique, phase difference of the baseline signal and the received acoustic signal may be used to determine the standard deviation (with respect to the mean), which may be normalized with respect to the total phase.

Figure 8A:
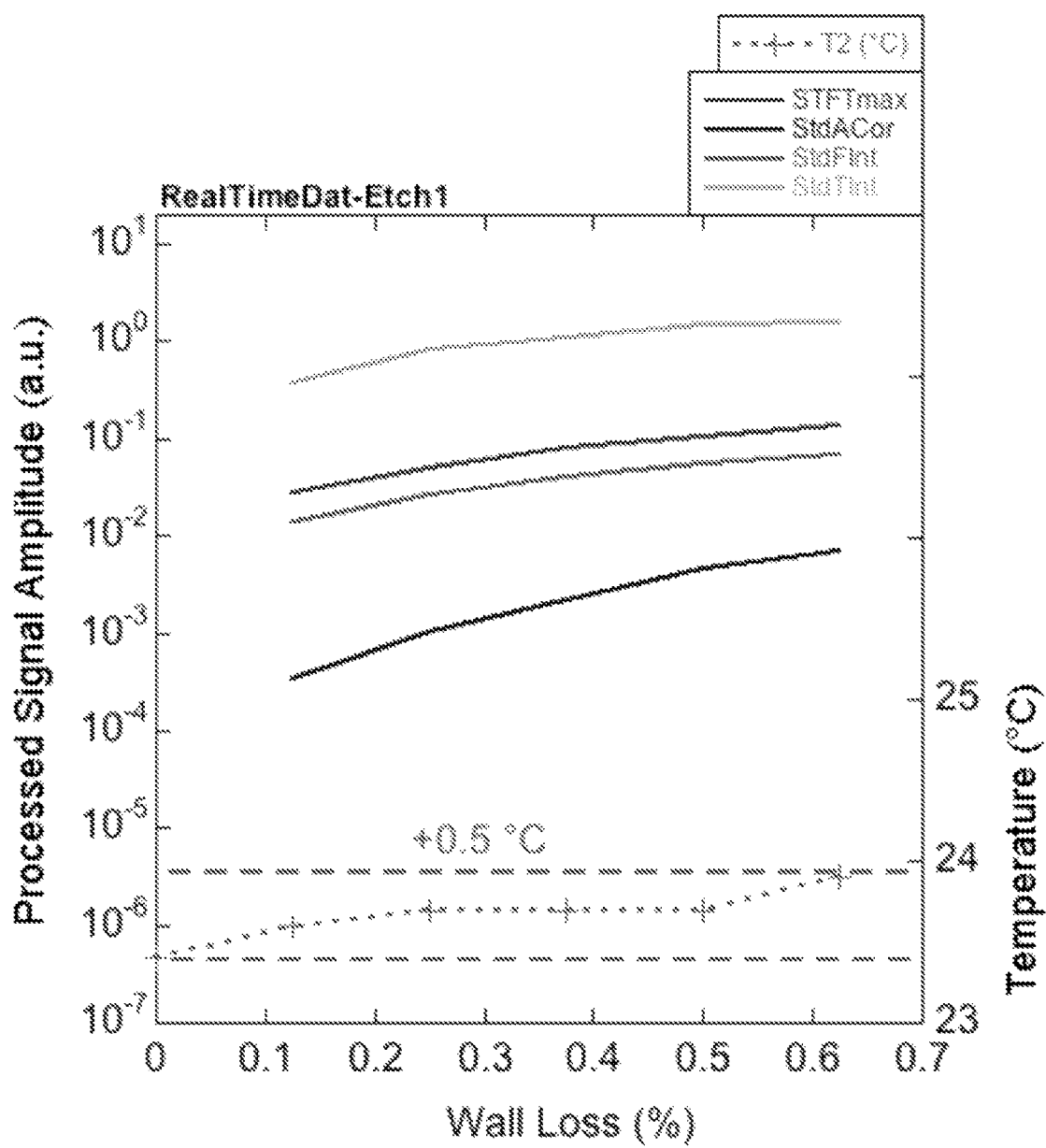
FIGS. 8A, 8B, and 8C illustrate example analyses of electrochemical etching.
Figure 8B:
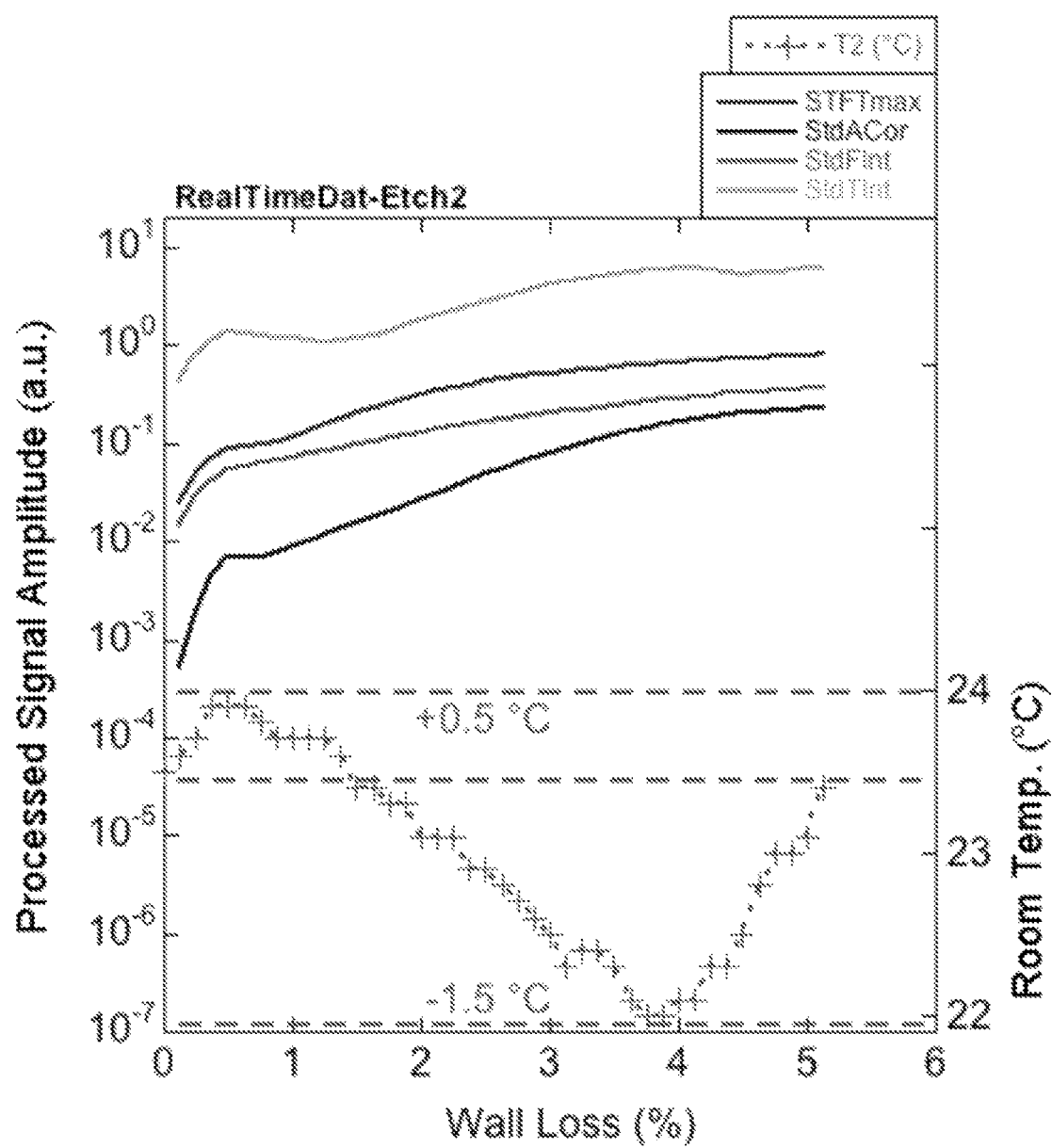
Figure 8C:
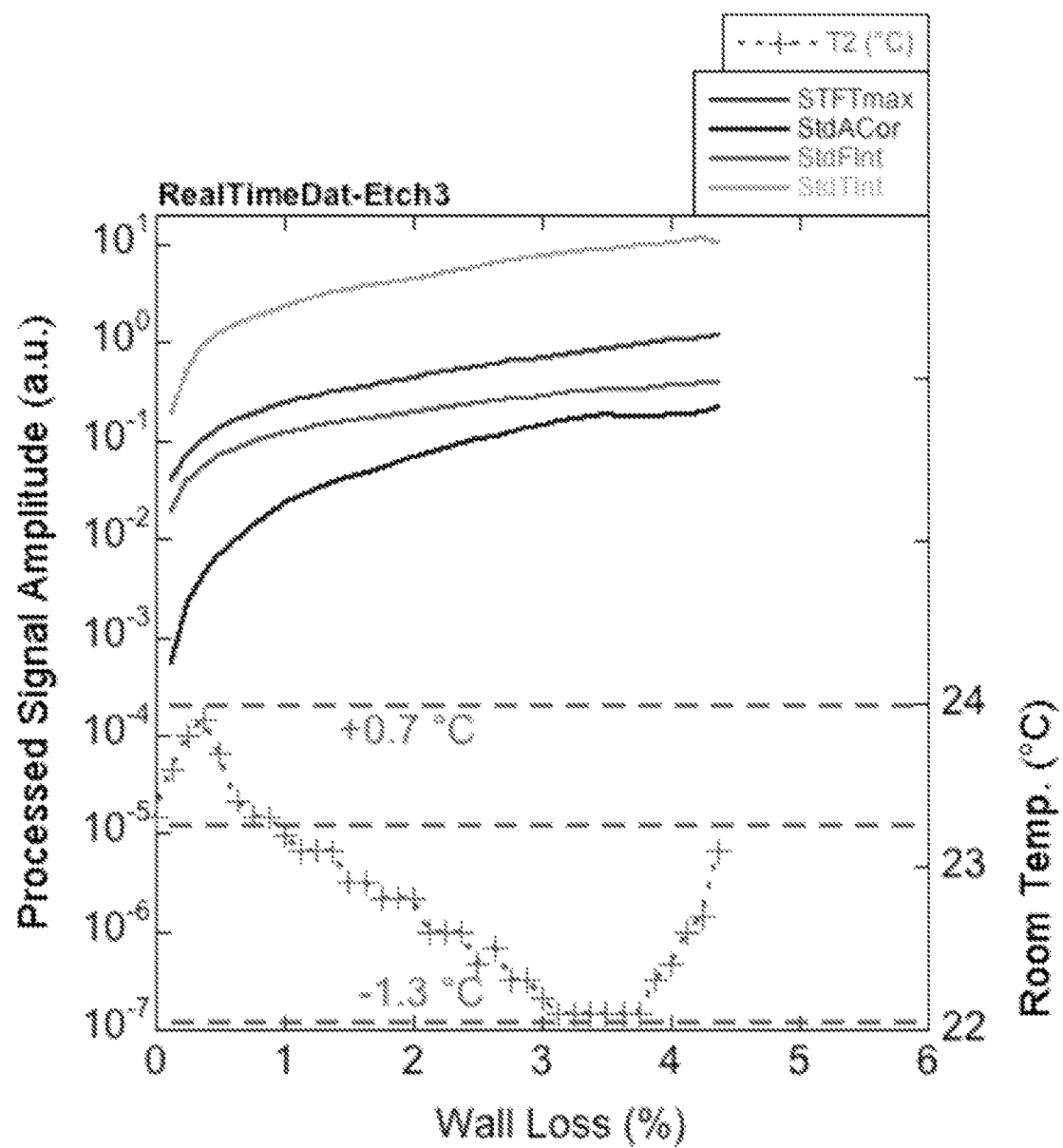

FIGS. 8A, 8B, and 8C illustrate example analyses of electrochemical etching. Electrochemical etching may include submerging a section of a structure, such as a pipe, in a solution and application of DC current between a counter-electrode in the solution and the pipe to electrochemically etch the pipe wall. The pipe may be etched using different conditions. For example, FIG. 8A illustrates an analysis of electrochemical etching with no stirring in the solution and a 0-degree rotation of sensor(s) (sensor(s) placed diametrically opposite of the etch), with about 0.6% total wall loss. FIG. 8B illustrates an analysis of electrochemical etching with no stirring in the solution and a 45-degree rotation of sensor(s), with about 5.2% total wall loss. FIG. 8C illustrates an analysis of electrochemical etching with no stirring in the solution, artificial texturing, and a 180-degree rotation of sensor(s) (sensor(s) placed on same plane as the etch), with about 4.4% total wall loss. FIGS. 8A, 8B, and 8C illustrate analyses of the change in the signal characteristics of the acoustic signal using four analytic techniques. FIGS. 8A-8C show that among the different analytic techniques, auto-correlation standard deviation technique provides results with greater difference in processed signal amplitude as a function of wall loss. That is, the results of the auto-correlation standard deviation technique changed more as a function of wall loss than other methods. Thus, the auto-correlation standard deviation technique may be more effective than other techniques to identify wall loss in a structure.

Figure 9:
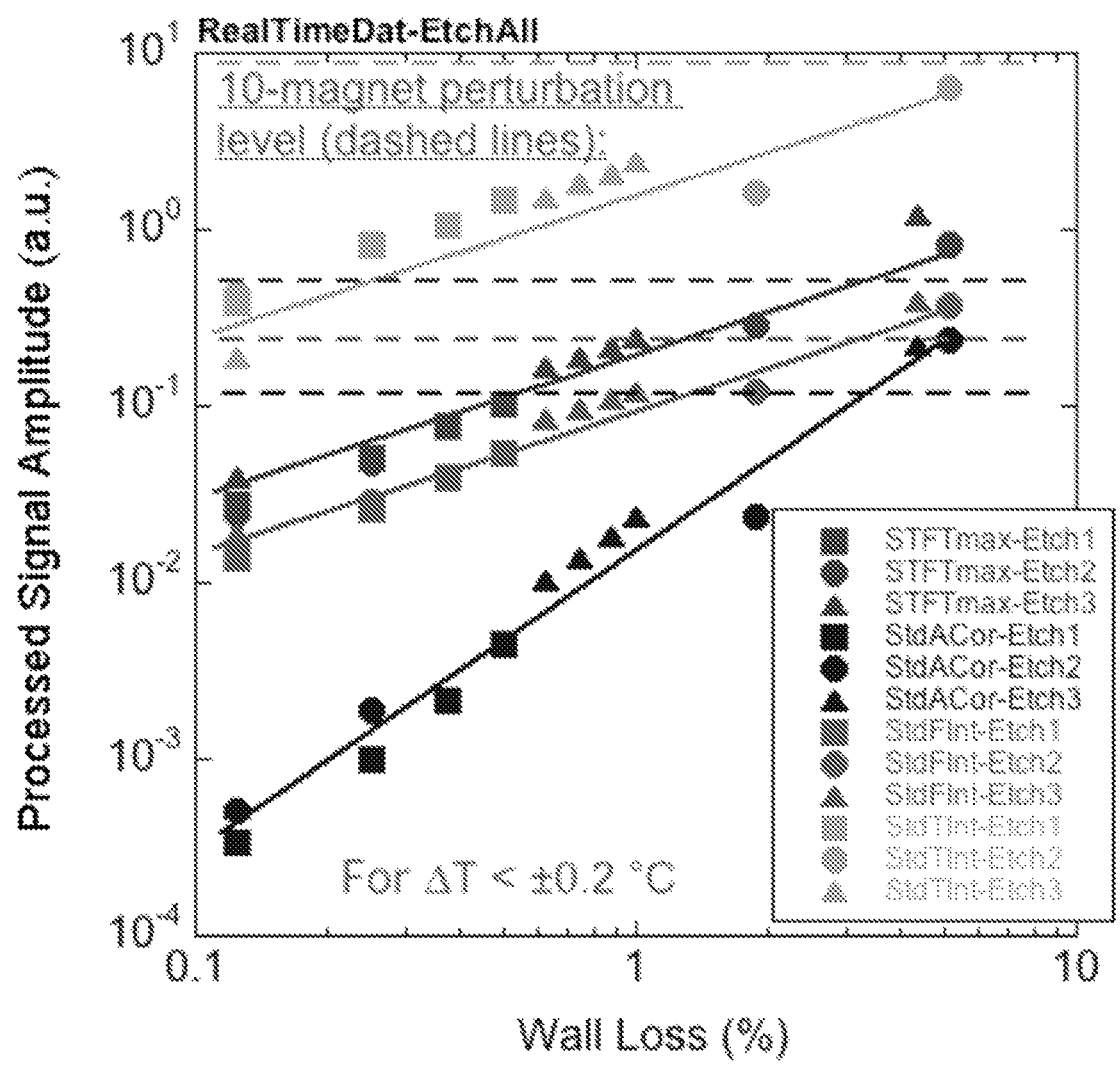
FIG. 9 illustrates example analysis of electrochemical etching in comparison with magnet perturbation.

FIG. 9 illustrates example analysis of electrochemical etching in comparison with magnet perturbation. Electrochemical etching may include etching of a two-inch diameter pipe. FIG. 9 illustrates analyses of the change in the signal characteristics of the acoustic signal for different etches using four analytic techniques. The results of four analytic techniques indicate monotonic increase of processed acoustic signal amplitude with wall loss. In FIG. 9, stirred etching may result in smoother surface (slightly weaker acoustic response) while non-stirred/textured etching may result in rougher surface (slightly stronger acoustic response). Around 4 to 5% material loss of the pipe may result in similar magnitude of perturbation as 10 attached magnets on the pipe.

Dashed lines provide a reference 10-magnet perturbation level, which may indicate sensitivity limits for different analyses. Dashed lines for different analytic techniques may illustrate the threshold level for which change to the structure may be identified. For example, while the results of StdTInt (Time-Integrated Standard Deviation) appear to have large signal amplitudes, the values of StdTInt results are below the corresponding threshold level and StdTInt may not be reliable to detect this type and magnitude of material loss. The results of STFTmax (Short-Time-Fourier-Transform Maximum), StdACor (Auto-Correlation Standard Deviation), and STdFInt (Frequency-Integrated Standard Deviation) are reliable to detect etching greater than about 3%. Thus, StdTInt may not be a reliable technique to detect material loss while other techniques may have similar sensitivity in detecting material loss. StdACor may have the largest change within reliable range of result and may be most appropriate to detect this type and magnitude of material loss.

Figure 10A:
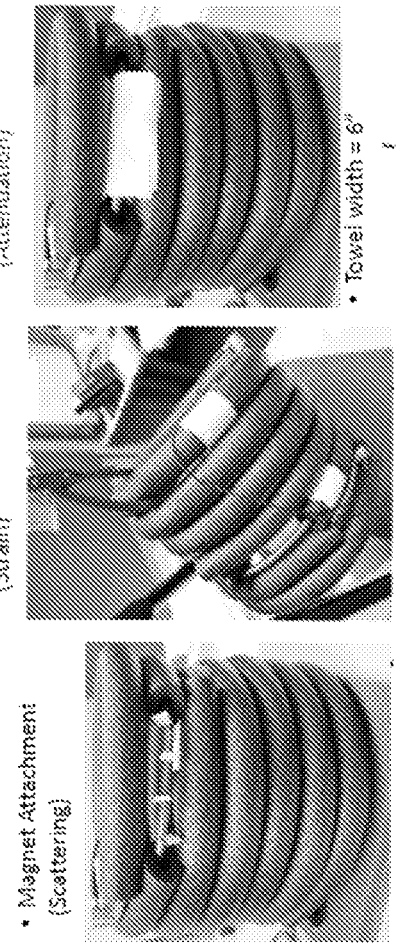
FIGS. 10A, 10B, 10C, and 10D illustrate example analyses of scattering, strain, and attenuation.
Figure 10A:
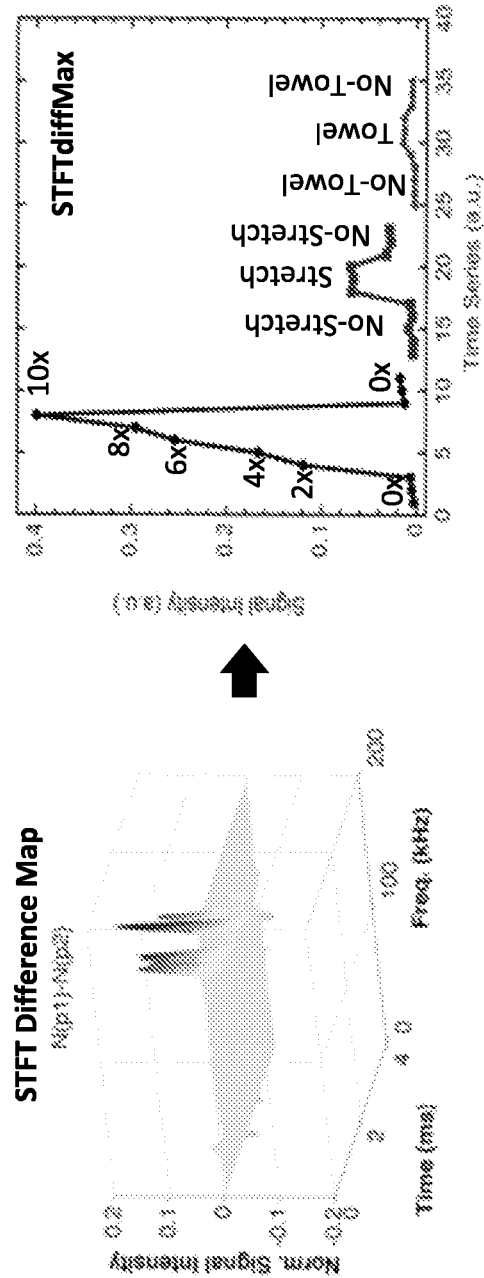

FIGS. 10A, 10B, 10C, and 10D illustrate example analyses of scattering, strain, and attenuation. FIG. 10 illustrate an example setup for scattering on coiled steel pipe using magnet attachment, an example setup for strain on coiled steel pipe using stretch with gravity, and an example setup for attenuation on coiled steel pipe using wet paper towel. The analytic techniques used to analyze the change in the signal characteristics of acoustic signal may include short-time-Fourier-transform difference maximum technique, time-integrated mean technique, and time-integrated standard deviation technique (shown in FIG. 10B), auto-correlation mean technique and auto-correlation standard deviation technique (shown in FIG. 10C), and phase shift mean technique and phase shift standard deviation technique (shown in FIG. 10D). The left curves may correspond to the results of scattering, the center curves may correspond to results of strain, and the right curves may correspond to results of attenuation. In FIG. 10A, the curves for STFTdiffMax show the signal strengths before perturbation (zero magnet, no stretch, no towel), during perturbation (different numbers of magnets, stretch, towel), and after perturbation (zero magnet, no stretch, no towel). The curves show whether the signal characteristics of the acoustic signal recovers (returns to pre-perturbation values) after the perturbation is removed. In FIG. 10A, the scattering curve has the largest change in signal intensity as magnets are added and removed. The stretch curve has weak but perceptible change in signal intensity. The attenuation curve has almost imperceptible change in signal intensity.

A combination of the analytic techniques shown in FIG. 10A may be used to improve identification of changes to a structure. For example, a combination of the analytic techniques shown in FIG. 10A may be used to improve the probability of attributing a change to a received acoustic signal where attenuation on a pipe (e.g., water accumulation) does not lead to much change in the signal characteristics, strain on the pipe leads to weak change in the signal characteristics, and scattering on the pipe (e.g., material loss or addition) leads to largest change in the signal characteristics.

Figure 10B:
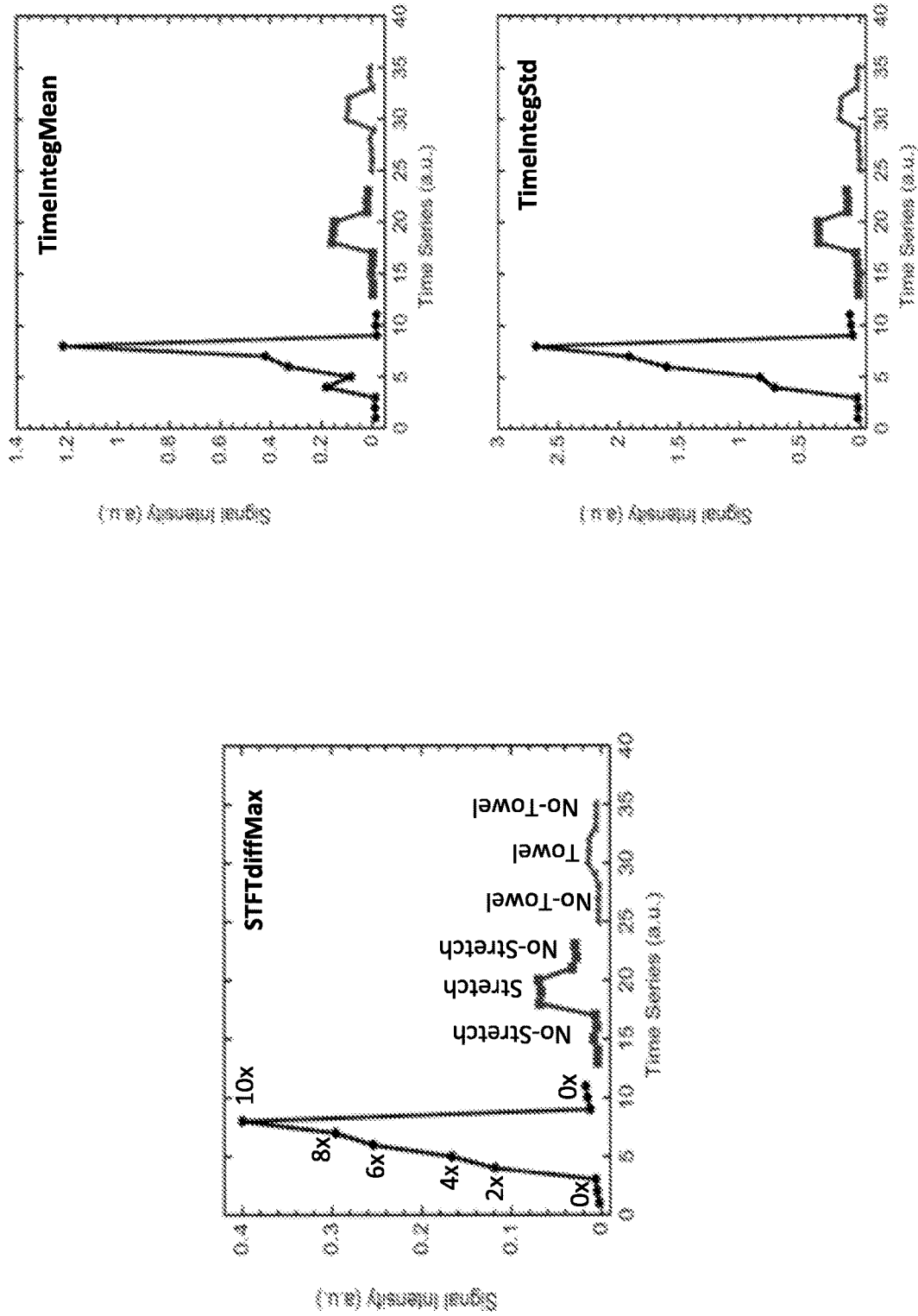

FIG. 10B illustrates comparison between results of short-time-Fourier-transform difference maximum technique, time-integrated mean technique, and time-integrated standard deviation technique. As shown in FIG. 10B, the largest change in signal characteristics for all analytic technique is due to scattering. Stretching results of the time-integrated mean technique and the time-integrated standard deviation technique are similar to the results of the short-time-Fourier-transform difference maximum technique. Towel results of time-integrated mean technique and the time-integrated standard deviation technique exhibit greater change in signal characteristics compared to the results of the short-time-Fourier-transform difference maximum technique. The time-integrated standard deviation technique may provide better observations of all components of perturbations compared to the short-time-Fourier-transform difference maximum technique.

A combination of the analytic techniques shown in FIGS. 10A-10B may be used to improve identification of changes to a structure. For example, a combination of the analytic techniques shown in FIGS. 10A-10B may be used to identify water accumulation effects based on the water accumulation effects showing up strongly within the results of the time-integrated mean technique while remaining relatively same/steady within the results of the short-time-Fourier-transform difference maximum technique.

FIG. 10O illustrates comparison between results of short-time-Fourier-transform difference maximum technique, auto-correlation mean technique, and auto-correlation standard deviation technique. The auto-correlation mean technique may provide a large response to scattering event. The stretch effect may be slightly reduced with respect to scattering event. The auto-correlation mean technique and the auto-correlation standard deviation technique may not provide perceptible effect for attenuation due to water accumulation.

Figure 10C:
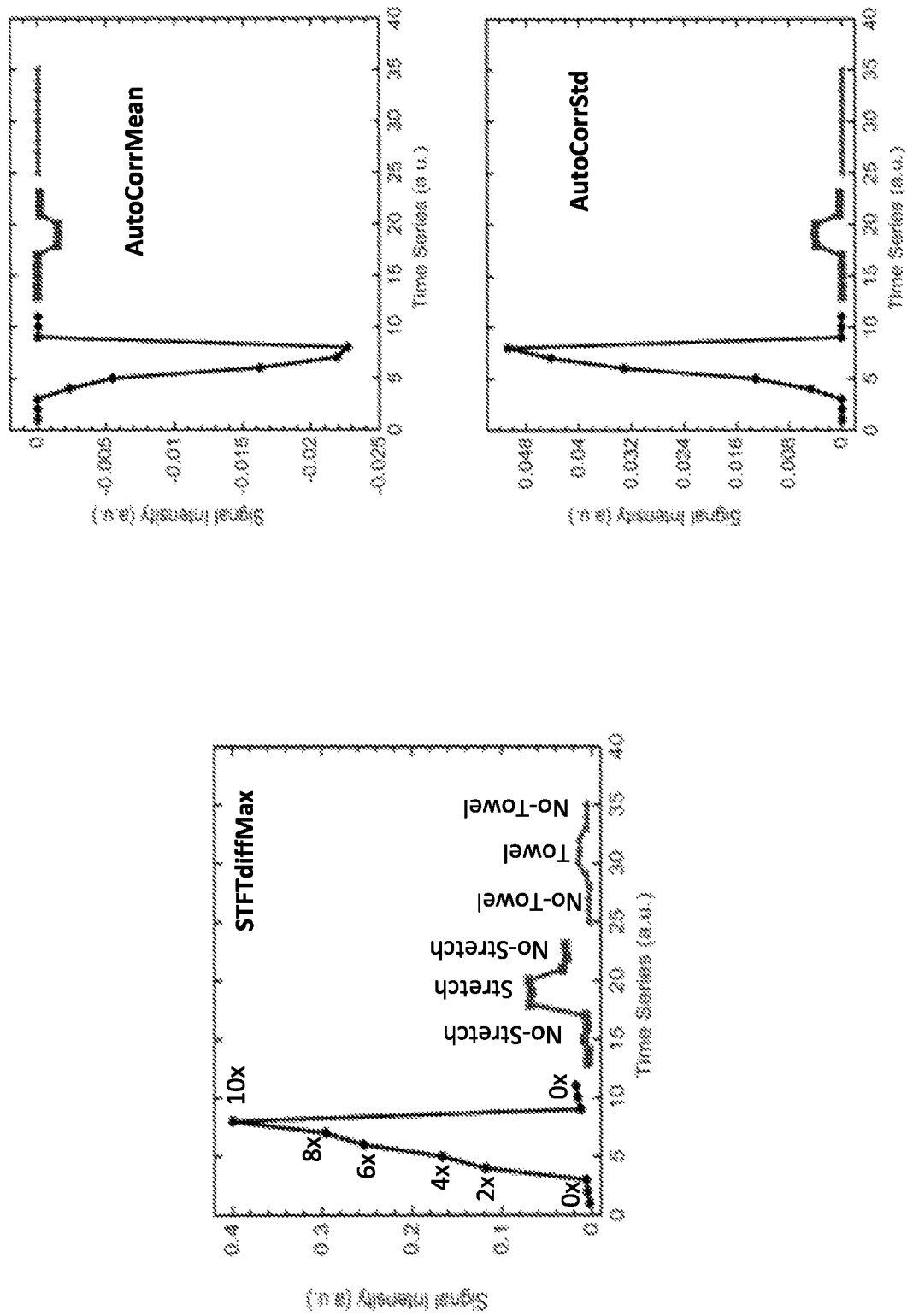

A combination of the analytic techniques shown in FIGS. 10A-10C may be used to improve identification of changes to a structure. For example, a combination of the analytic techniques shown in FIGS. 10A-10C may be used to identify whether a change in signal characteristics of an acoustic signal is due to water accumulation or not based on perceptible effects in the time-integrated mean technique and/or the time-integrated standard deviation technique and no perceptible effects in the auto-correlation mean technique and/or the auto-correlation standard deviation technique. As another example, the large response of the auto-correlation mean technique may be used to identify scattering events.

Figure 10D:
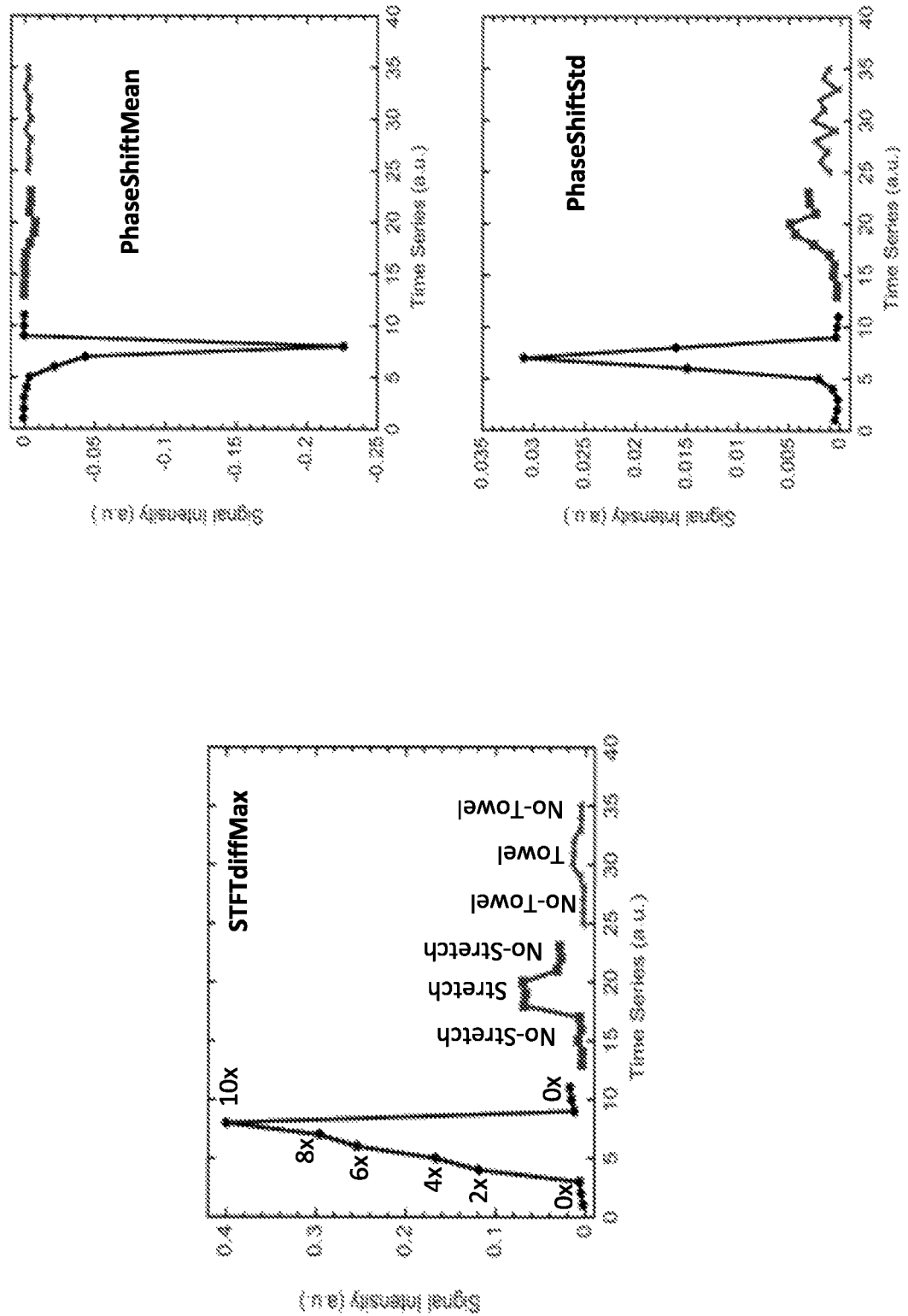

FIG. 10D illustrates comparison between results of short-time-Fourier-transform difference maximum technique, phase shift mean technique, and phase shift standard deviation technique. The results of the phase shift mean technique and the phase shift standard deviation technique may show strong response to scattering events. The results of the phase shift mean technique and the phase shift standard deviation technique may allow for differentiation between strong scattering (multiple magnets) and weak scattering and attenuation. With respect to the phase shift mean technique, the scattering effects may be super-linear (smaller effect at small number of magnets, larger effect at larger number of magnets), stretch effect may be strongly reduced, and the towel effect may be strongly suppressed. With respect to the phase shift standard deviation technique, magnet effects may be non-linear and noisy, stretch effect may be slightly reduced but noisy, and the towel effect may be strongly reduced but very noisy. The phase-shift mean technique may allow for better differentiation of time-of arrival changes in acoustic signal transmission, which may be expected to be more sensitive to multiple scattering events and/or temperature effects.

A combination of the analytic techniques shown in FIGS. 10A-10D may be used to improve identification of changes to a structure. For example, a combination of the analytic techniques shown in FIGS. 10A-10D may be used to identify whether the observed effect is due to scattering, strain, or attenuation based on distinctive responses of the analytic techniques to different structure perturbations.

Figure 11A:
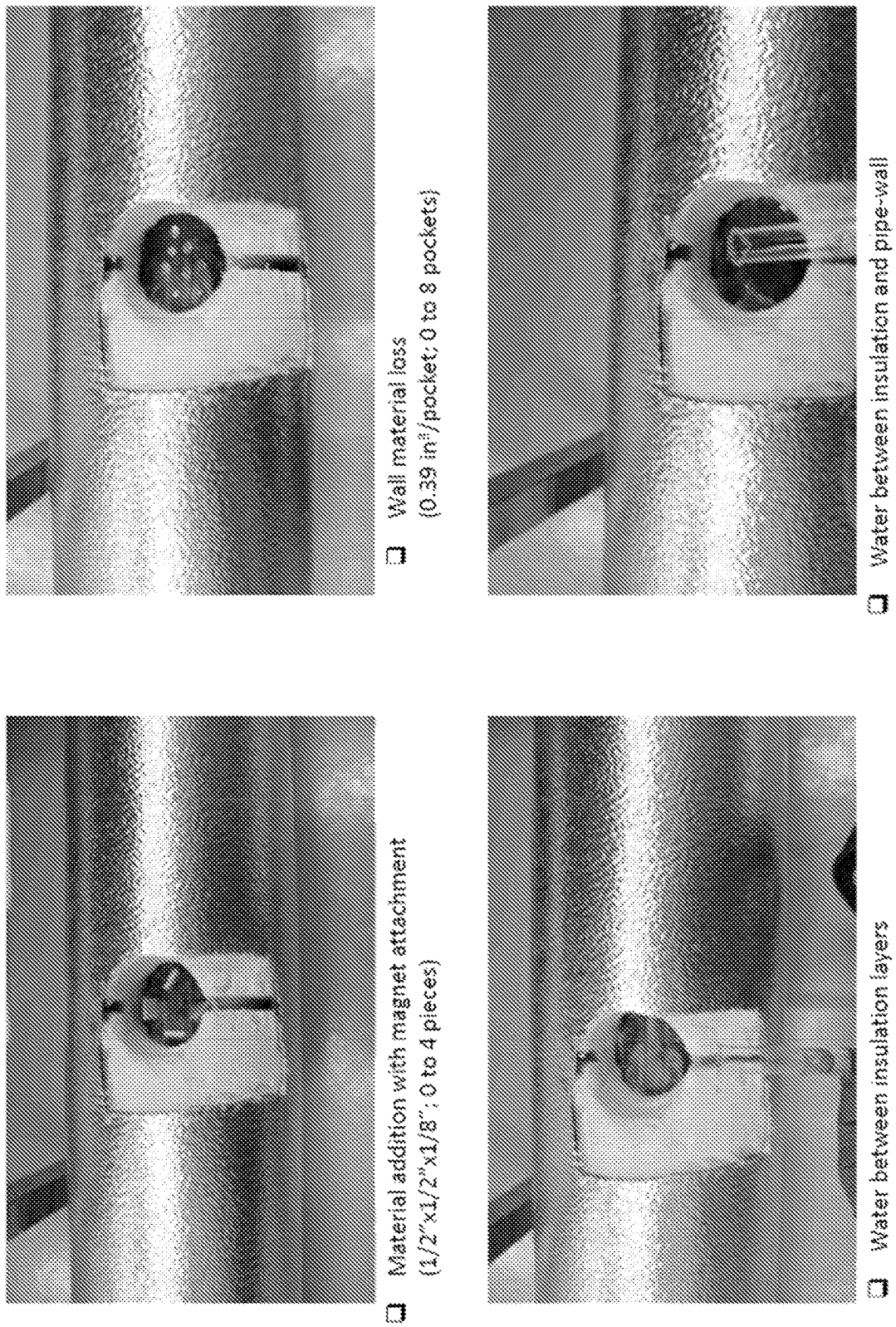
FIG. 11A illustrates example scenarios for changes to a pipe.

FIG. 11A illustrates example scenarios for changes to a pipe, and FIG. 11B-11E illustrate example analyses of changes to a pipe. As shown in FIG. 11A, changes to a pipe may include material addition with magnet attachment, wall material loss with drilled pockets, water between insulation layers of the pipe, and water between insulation and pipe-wall. FIGS. 11B-11E illustrates results of different analytic techniques based on changes to the pipe.

Figure 11B:
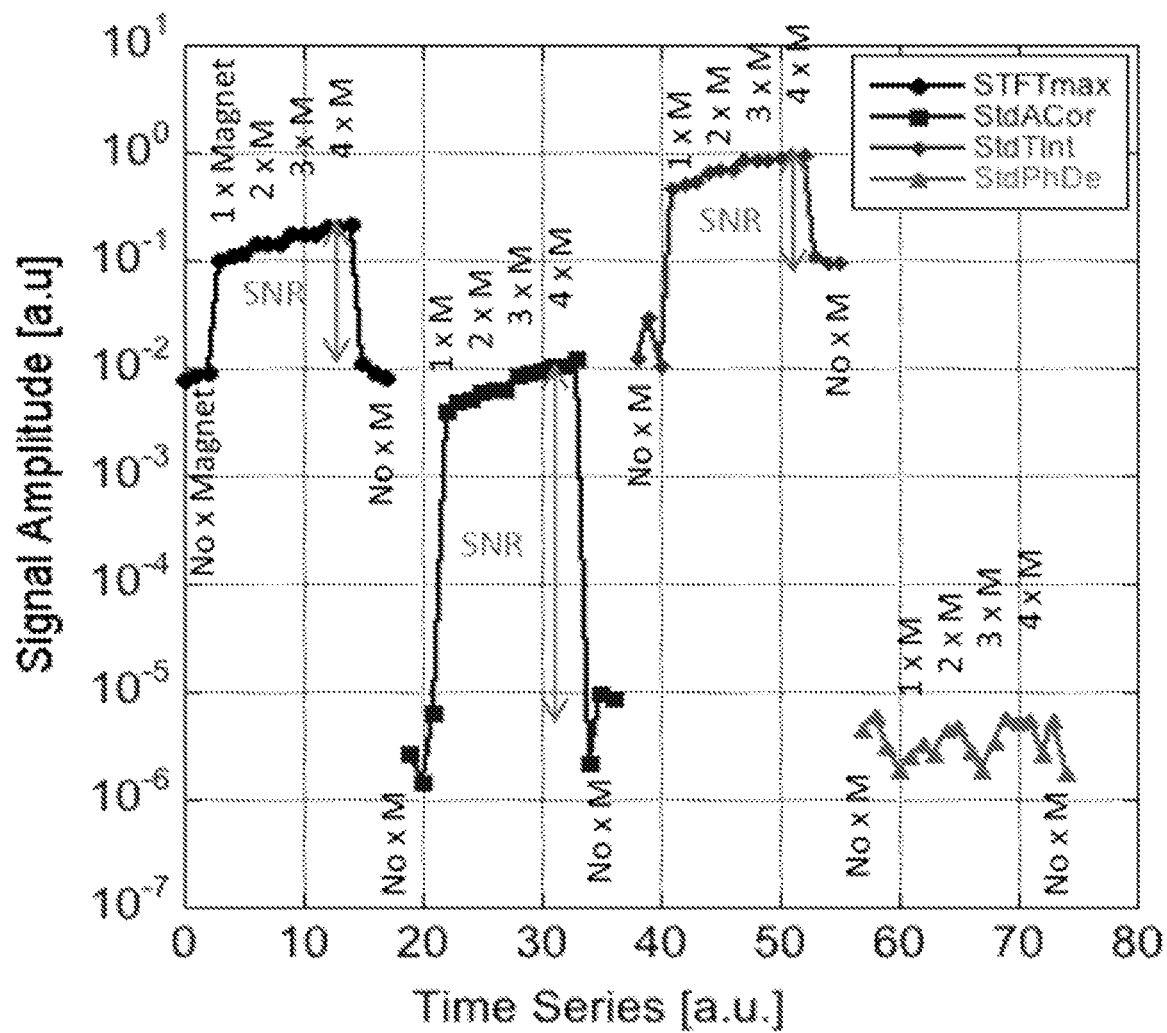
FIGS. 11B, 11C, 11D, and 11E illustrate example analyses of changes to a pipe.

FIG. 11B illustrates results of different analytic techniques based on material addition (magnet attachment) to the pipe. The time series data may indicate the sensitivity (signal-to-noise radio) and the noise floor of individual analytic techniques. In FIG. 11B, the StdACor technique may be the most sensitive (has the largest SNR) and the StdPhDe may be least sensitive to detect material addition on the pipe wall.

Figure 11C:
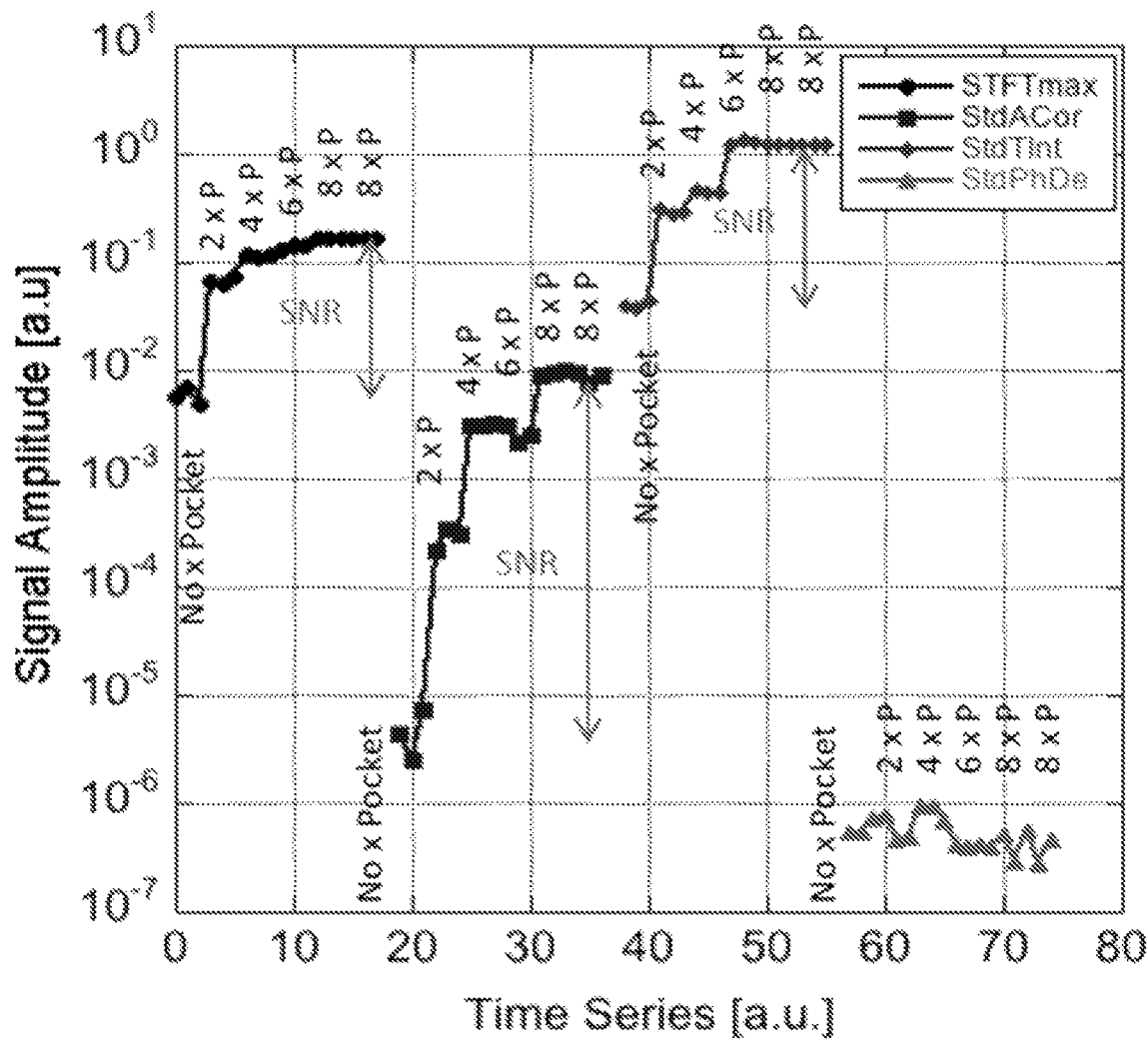

FIG. 11C illustrates results of different analytic techniques based on material loss (drilled pockets) of the pipe. Each drilled pocket may correspond to about 0.39 cubic inch volume removal from the pipe wall in a two-inch diameter opening of the insulation. In terms of percentage volume change, one pocket may correspond to about −0.2% (local pipe wall volume change with respect to the exposed two-inch diameter area) and about −8 ppm (total pipe wall volume change). In FIG. 11C, the StdACor technique may be most sensitive (has the largest SNR) and StdPhDe may be least sensitive to detect material loss of the pipe. Comparison of the results shown in FIGS. 11B and 11C show that material addition and material loss led to similar magnitude of effect in the different analytic techniques.

Figure 11D:
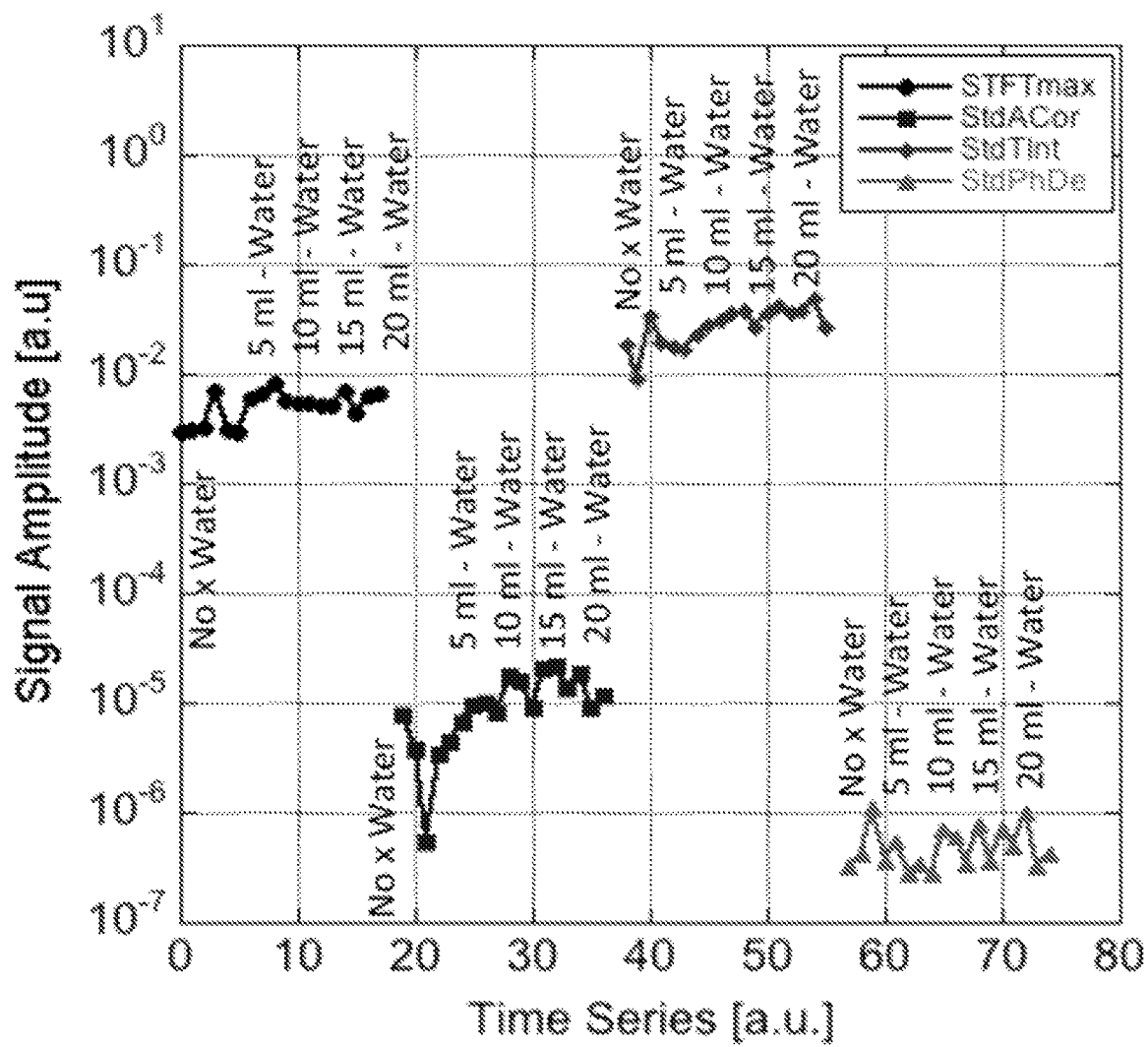
Figure 11E:
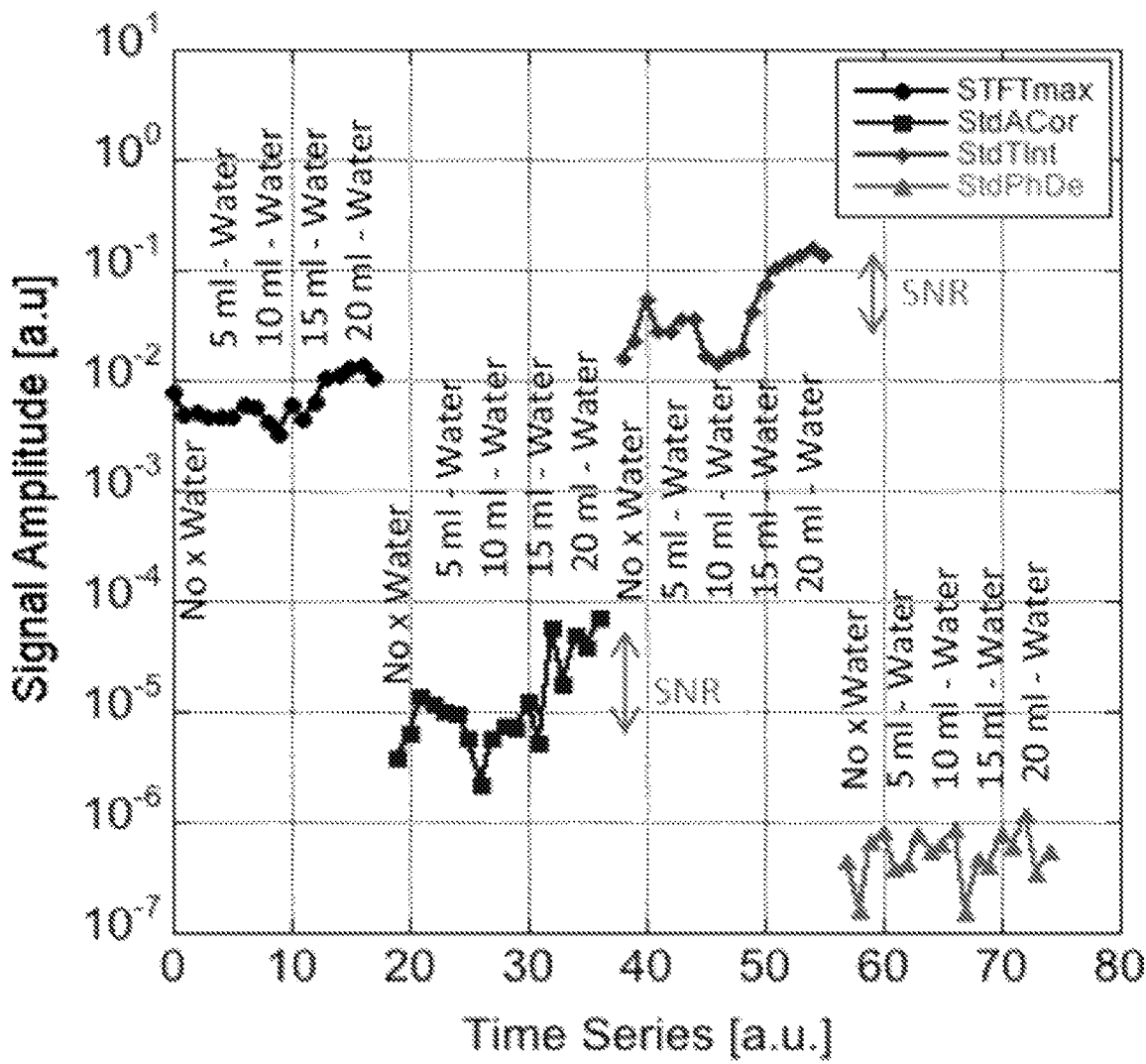

FIGS. 11D-11E illustrate results of different analytic techniques based on presence of water. FIG. 11D illustrates results of water between two insulation layers and FIG. 11E illustrates results of water between insulation and pipe wall. In FIG. 11E, the StdACor and StdTInt techniques may be most sensitive (has the largest SNR) to the presence of water on pipe outer wall. This effect may be much weaker than material addition/loss effects, as shown in FIGS. 11B-11C.

FIG. 11D illustrates presence of water within insulation layers may not result in appreciable effect for the analytic techniques.

Figure 12:
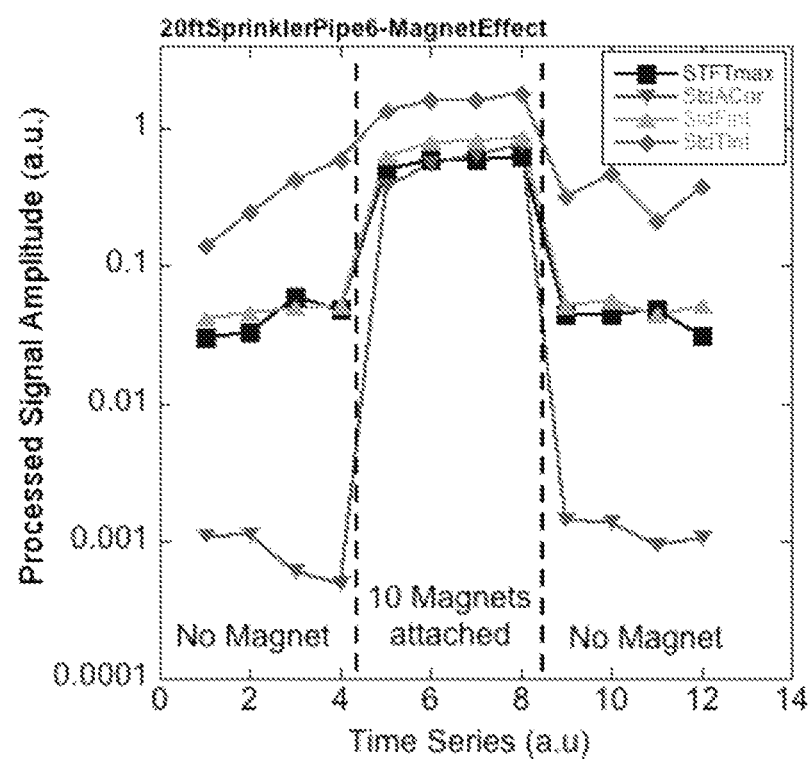
FIG. 12 illustrates example analyses of scattering.

FIGS. 12-15 illustrates example analyses of signal characteristics of acoustics signals traveling along a pipe. FIG. 12 illustrates sensitivity of different analytic techniques based on attaching and removing magnets from pipes. In FIG. 12, the StdACor technique may be most sensitive (close to 1000 times the background level) to magnet perturbations while the sensitivities of the STFTmax and STDFInt techniques may be significantly lower (about 10 times the background level).

Figure 13:
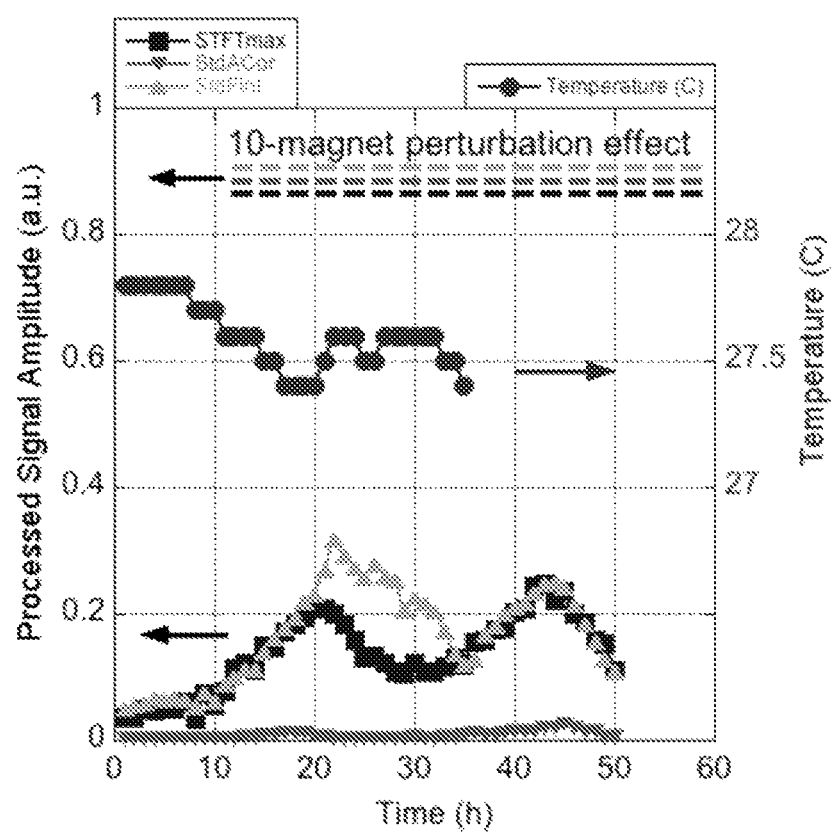
FIG. 13 illustrates example analyses of scattering in comparison with temperature effects.

FIG. 13 illustrates selectivity of different analytic techniques for monitoring amplitudes of signals traveling along a pipe in the presence of facility noise and temperature fluctuations. In FIG. 13, the StdACor technique may be most selective (about 50 times above background fluctuations) and show the most distinct response to different perturbations based on scattering effect over a span of 50 hours and a temperature change of 0.5 degree Celsius. FIG. 13 shows possible correlation between the pipe temperature and background level for the different analytic techniques. At low signal levels, the results of the analytic techniques may not provide identification of the scattering effect with high confidence. The response measured by these analytic techniques at the low levels may be due to other effects, such as temperature fluctuations.

Figure 14:
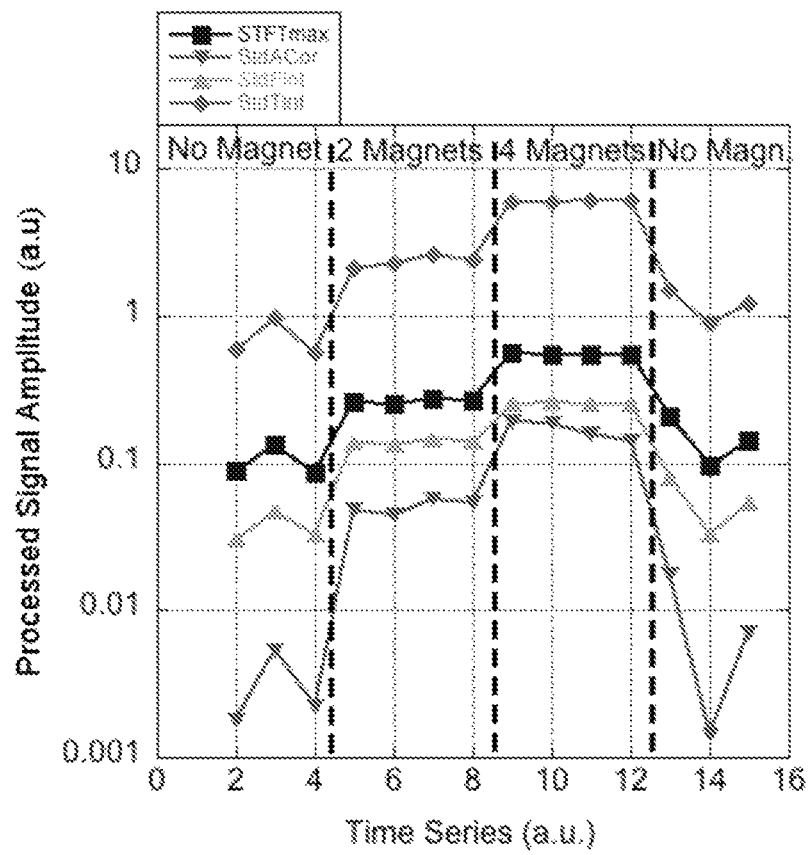
FIG. 14 illustrates example analyses of scattering.

FIG. 14 illustrates sensitivity of different analytic techniques based on attaching and removing magnets with clamps from pipes. In FIG. 14, the StdACor technique may be most sensitive (more than 10 times the background level) for 4-magnet perturbation, while sensitivities of other analytic techniques may be significantly lower (about 2 to 4 times the background level).

Figure 15:
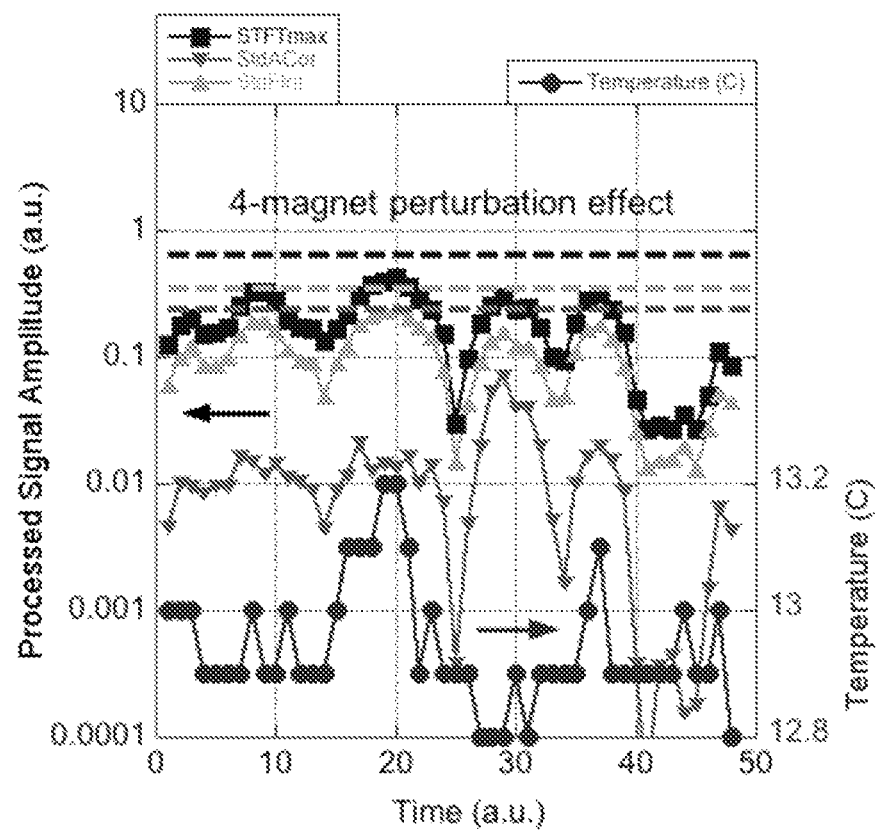
FIG. 15 illustrates example analyses of scattering in comparison with temperature effects.

FIG. 15 illustrates selectivity of different analytic techniques for monitoring amplitudes of signals traveling along a pipe in the presence of flowing water, facility noise, and temperature fluctuations. In FIG. 15, the StdACor technique may be most selective (about 10 times above the background fluctuations) and show the most distinct response to 4-magnet perturbation effect and a temperature change of 0.4 degree Celsius. FIG. 15 shows that the correlation between the pipe temperature and background signal levels may be difficult to discern in this case. The results of different analytic techniques shown in FIG. 15 may be close to their sensitivity limits.

Implementations of the disclosure may be made in hardware, firmware, software, or any suitable combination thereof. Aspects of the disclosure illustrated in FIG. 1 may be implemented as instructions stored on a machine-readable medium, which may be read and executed by one or more processors. A machine-readable medium may include any mechanism for storing or transmitting information in a form readable by a machine (e.g., a computing device). For example, a tangible (non-transitory) machine-readable storage medium may include read-only memory, random access memory, magnetic disk storage media, optical storage media, flash memory devices, and others, and a machine-readable transmission media may include forms of propagated signals, such as carrier waves, infrared signals, digital signals, and others. Firmware, software, routines, or instructions may be described herein in terms of specific exemplary aspects and implementations of the disclosure, and performing certain actions.

In some implementations, some or all of the functionalities attributed herein to the system 10 in FIG. 1 may be provided by external resources not included in the system 10. External resources may include hosts/sources of information, computing, and/or processing and/or other providers of information, computing, and/or processing outside of the system 10.

Although the processor 11, the electronic storage 13, the acoustic transmission transducer 14, and the acoustic reception transducer 15 are shown to be connected to the interface 12 in FIG. 1, any communication medium may be used to facilitate direct and/or indirect interaction between any components of the system 10. One or more components of the system 10 may communicate with each other through hard-wired communication, wireless communication, or both. For example, one or more components of the system 10 may communicate with each other through a network. For example, the processor 11 may wirelessly communicate with the electronic storage 13. By way of non-limiting example, wireless communication may include one or more of radio communication, Bluetooth communication, Wi-Fi communication, cellular communication, infrared communication, or other wireless communication. Other types of communications are contemplated by the present disclosure.

Although the processor 11 is shown in FIG. 1 as a single entity, this is for illustrative purposes only. In some implementations, the processor 11 may comprise a plurality of processing units. These processing units may be physically located within the same device, or the processor 11 may represent processing functionality of a plurality of devices operating in coordination. The processor 11 may be separate from and/or be part of one or more components of the system 10. The processor 11 may be configured to execute one or more components by software; hardware; firmware; some combination of software, hardware, and/or firmware; and/or other mechanisms for configuring processing capabilities on the processor 11.

It should be appreciated that although computer program components are illustrated in FIG. 1 as being co-located within a single processing unit, in implementations in which processor 11 comprises multiple processing units, one or more of computer program components may be located remotely from the other computer program components. While computer program components are described as performing or being configured to perform operations, computer program components may comprise instructions which may program processor 11 and/or system 10 to perform the operation.

While computer program components are described herein as being implemented via processor 11 through machine-readable instructions 100, this is merely for ease of reference and is not meant to be limiting. In some implementations, one or more functions of computer program components described herein may be implemented via hardware (e.g., dedicated chip, field-programmable gate array) rather than software. One or more functions of computer program components described herein may be software-implemented, hardware-implemented, or software and hardware-implemented The description of the functionality provided by the different computer program components described herein is for illustrative purposes, and is not intended to be limiting, as any of computer program components may provide more or less functionality than is described. For example, one or more of computer program components may be eliminated, and some or all of its functionality may be provided by other computer program components. As another example, processor 11 may be configured to execute one or more additional computer program components that may perform some or all of the functionality attributed to one or more of computer program components described herein.

The electronic storage media of the electronic storage 13 may be provided integrally (i.e., substantially non-removable) with one or more components of the system 10 and/or as removable storage that is connectable to one or more components of the system 10 via, for example, a port (e.g., a USB port, a Firewire port, etc.) or a drive (e.g., a disk drive, etc.). The electronic storage 13 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. The electronic storage 13 may be a separate component within the system 10, or the electronic storage 13 may be provided integrally with one or more other components of the system 10 (e.g., the processor 11). Although the electronic storage 13 is shown in FIG. 1 as a single entity, this is for illustrative purposes only. In some implementations, the electronic storage 13 may comprise a plurality of storage units. These storage units may be physically located within the same device, or the electronic storage 13 may represent storage functionality of a plurality of devices operating in coordination.

Figure 2:
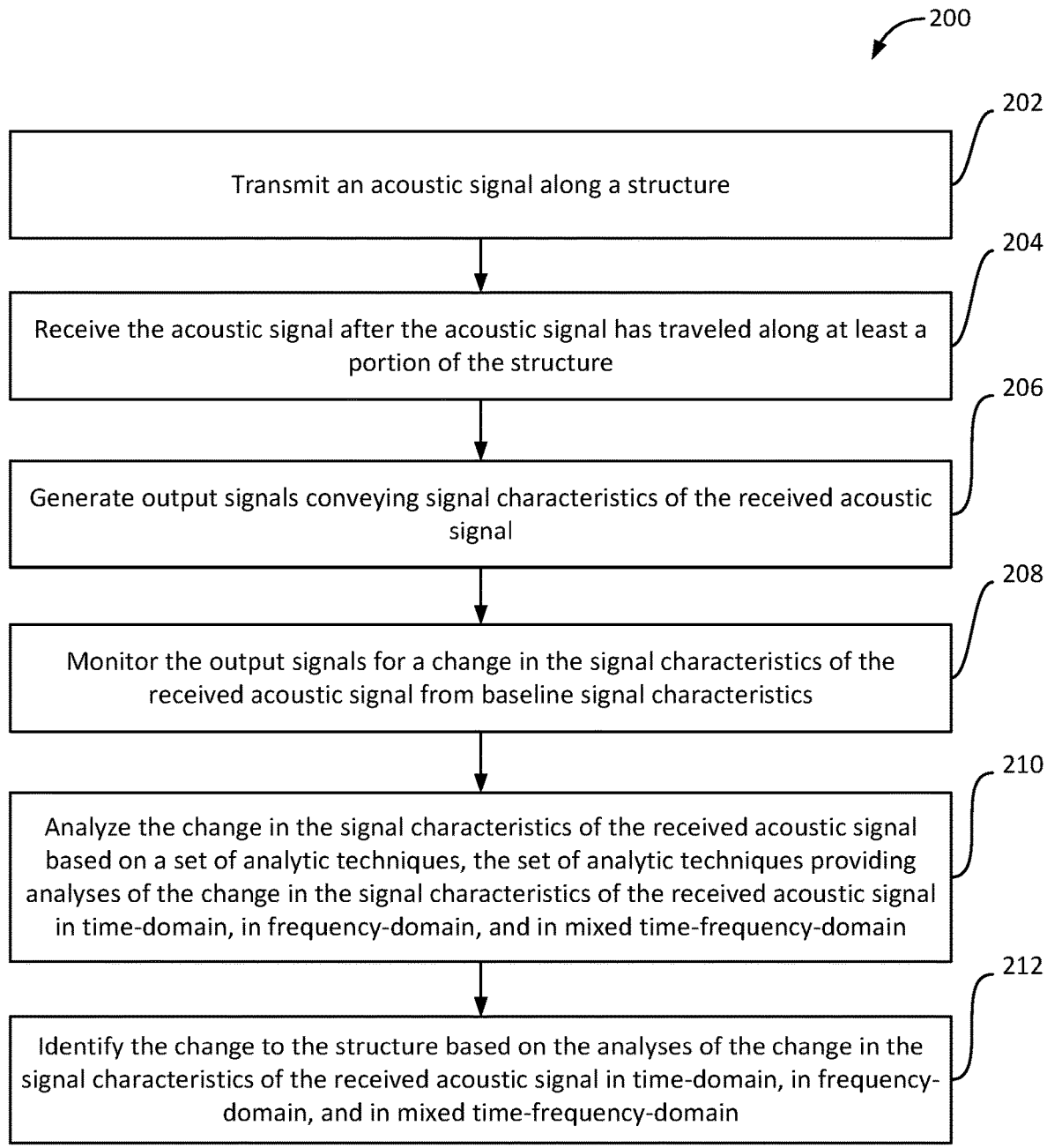
FIG. 2 illustrates an example method for identifying changes to a structure.

FIG. 2 illustrates method 200 for identifying changes to a structure. The operations of method 200 presented below are intended to be illustrative. In some implementations, method 200 may be accomplished with one or more additional operations not described, and/or without one or more of the operations discussed. In some implementations, two or more of the operations may occur substantially simultaneously.

In some implementations, one or more operations of the method 200 may be implemented in one or more processing devices (e.g., a digital processor, an analog processor, a digital circuit designed to process information, a central processing unit, a graphics processing unit, a microcontroller, an analog circuit designed to process information, a state machine, and/or other mechanisms for electronically processing information). The one or more processing devices may include one or more devices executing some or all of the operations of method 200 in response to instructions stored electronically on one or more electronic storage media. The one or more processing devices may include one or more devices configured through hardware, firmware, and/or software to be specifically designed for execution of one or more of the operations of method 200.

Referring to FIG. 2 and method 200, at operation 202, an acoustic signal may be transmitted along a structure. In some implementation, operation 202 may be performed by a component the same as or similar to the acoustic transmission transducer 14 (Shown in FIG. 1 and described herein).

At operation 204, the acoustic signal may be received after the acoustic signal has traveled along at least a portion of the structure. In some implementation, operation 204 may be performed by a component the same as or similar to the acoustic reception transducer 15 (Shown in FIG. 1 and described herein).

At operation 206, output signals conveying signal characteristics of the received acoustic signal may be generated. In some implementation, operation 206 may be performed by a component the same as or similar to the acoustic reception transducer 15 (Shown in FIG. 1 and described herein).

At operation 208, the output signals may be monitored for a change in the signal characteristics of the received acoustic signal from baseline signal characteristics. The change in the signal characteristics of the received acoustic signal may be caused by a change to the structure. In some implementation, operation 208 may be performed by a component the same as or similar to the monitor component 102 (Shown in FIG. 1 and described herein).

At operation 210, the change in the signal characteristics of the received acoustic signal may be analyzed based on a set of analytic techniques and/or other information. The set of analytic techniques may provide analyses of the change in the signal characteristics of the received acoustic signal in time-domain, in frequency-domain, in mixed time-frequency-domain, and/or other domains. In some implementation, operation 210 may be performed by a component the same as or similar to the analysis component 104 (Shown in FIG. 1 and described herein).

At operation 212, the change to the structure may be identified based on the analyses of the change in the signal characteristics of the received acoustic signal in time-domain, in frequency-domain, in mixed time-frequency-domain, and/or in other domains, and/or other information. In some implementation, operation 212 may be performed by a component the same as or similar to the identification component 106 (Shown in FIG. 1 and described herein).

Although the system(s) and/or method(s) of this disclosure have been described in detail for the purpose of illustration based on what is currently considered to be the most practical and preferred implementations, it is to be understood that such detail is solely for that purpose and that the disclosure is not limited to the disclosed implementations, but, on the contrary, is intended to cover modifications and equivalent arrangements that are within the spirit and scope of the appended claims. For example, it is to be understood that the present disclosure contemplates that, to the extent possible, one or more features of any implementation can be combined with one or more features of any other implementation.

What is claimed is:

1. A system for identifying changes to a structure, the system comprising:
    an acoustic transmission transducer configured to transmit an acoustic signal along the structure;
    an acoustic reception transducer configured (i) to receive the acoustic signal after the acoustic signal has traveled along at least a portion of the structure, and (ii) to generate output signals conveying signal characteristics of the received acoustic signal; and
    one or more processors configured to:
        monitor the output signals for a change in the signal characteristics of the received acoustic signal from baseline signal characteristics, the change in the signal characteristics of the received acoustic signal caused by a change to the structure;
        analyze the change in the signal characteristics of the received acoustic signal based on a set of analytic techniques, the set of analytic techniques providing analyses of the change in the signal characteristics of the received acoustic signal in time-domain, in frequency-domain, and in mixed time-frequency-domain, wherein the analyses of the change in the signal characteristics of the received acoustic signal in time-domain, in frequency-domain, and in mixed time-frequency-domain have different sensitivities to different sources of changes to the structure and enables differentiation between the different sources of changes to the structure, the different sources of changes to the structure including different types or different causes of changes to the structure, further wherein:
            the analysis of the change in the signal characteristics of the received acoustic signal in time-domain includes determination of a first pattern of changes in time delay and/or phase shift of the signal characteristics of the received acoustic signal from the baseline signal characteristics,
            the analysis of the change in the signal characteristics of the received acoustic signal in frequency-domain includes determination of a second pattern of changes in frequency-domain signal intensity of the signal characteristics of the received acoustic signal from the baseline signal characteristics, the frequency-domain signal intensity of the signal characteristics determined based on signal intensity as a function of frequency; and
            the analysis of the change in the signal characteristics of the received acoustic signal in mixed time-frequency-domain includes determination of a third pattern of changes in mixed time-frequency signal intensity of the signal characteristics of the received acoustic signal from the baseline signal characteristics, the mixed time-frequency signal intensity of the signal characteristics determined based on signal intensity as a function of frequency and time; and
        identify the change to the structure based on the analyses of the change in the signal characteristics of the received acoustic signal in time-domain, in frequency-domain, and in mixed time-frequency-domain, wherein the identification of the change to the structure based on the analyses of the change in the signal characteristics of the received acoustic signal in time-domain, in frequency-domain, and in mixed time-frequency-domain includes identification of a type or a cause of the change to the structure based on the first pattern of changes in time delay and/or phase shift of the signal characteristics, the second pattern of changes in frequency-domain signal intensity of the signal characteristics, and the third pattern of changes in mixed time-frequency signal intensity of the signal characteristics.

2. The system of claim 1, wherein the set of analytic techniques includes:
    for the analyses of the change in the signal characteristics of the received acoustic signal in time-domain, a time-shift mean technique, a time-shift standard deviation technique, and/or a piecewise phase correction technique;
    for the analyses of the change in the signal characteristics of the received acoustic signal in frequency-domain, a time-integrated mean technique and/or a time-integrated standard deviation technique; and
    for the analyses of the change in the signal characteristics of the received acoustic signal in mixed time-frequency-domain, a short-time-Fourier-transform difference maximum technique, an auto-correlation mean technique, and/or an auto-correlation standard deviation technique.

3. The system of claim 1, wherein the differentiation between the different sources of changes to the structure includes differentiation between material loss, material conversion, or material addition.

4. The system of claim 3, wherein the material loss includes pitting, cracking, or fracturing of the structure, the material conversion includes corrosion of the structure, and the material addition includes material migration, material accumulation, or material adsorption.

5. The system of claim 1, wherein the identification of the type or the cause of the change to the structure includes classification of the type or the cause of the change to the structure, the classification of the type or the cause of the change associated with a confidence level.

6. The system of claim 1, wherein the structure includes a metallic, rigid structure.

7. The system of claim 6, wherein the metallic, rigid structure includes a pipe, a vessel, or a container.

8. A method for identifying changes to a structure, the method performed by a system comprising an acoustic transmission transducer, an acoustic reception transducer, and one or more processors, the method comprising:

transmitting, by the acoustic transmission transducer, an acoustic signal along the structure;

receiving, by the acoustic reception transducer, the acoustic signal after the acoustic signal has traveled along at least a portion of the structure;

generating, by the acoustic reception transducer, output signals conveying signal characteristics of the received acoustic signal;

monitoring, by the one or more processors, the output signals for a change in the signal characteristics of the received acoustic signal from baseline signal characteristics, the change in the signal characteristics of the received acoustic signal caused by a change to the structure;

analyzing, by the one or more processors, the change in the signal characteristics of the received acoustic signal based on a set of analytic techniques, the set of analytic techniques providing analyses of the change in the signal characteristics of the received acoustic signal in time-domain, in frequency-domain, and in mixed time-frequency-domain, wherein the analyses of the change in the signal characteristics of the received acoustic signal in time-domain, in frequency-domain, and in mixed time-frequency-domain have different sensitivities to different sources of changes to the structure and enables differentiation between the different sources of changes to the structure, the different sources of changes to the structure including different types or different causes of changes to the structure, further wherein:

the analysis of the change in the signal characteristics of the received acoustic signal in time-domain includes determination of a first pattern of changes in time delay and/or phase shift of the signal characteristics of the received acoustic signal from the baseline signal characteristics, the analysis of the change in the signal characteristics of the received acoustic signal in frequency-domain includes determination of a second pattern of changes in frequency-domain signal intensity of the signal characteristics of the received acoustic signal from the baseline signal characteristics, the frequency-domain signal intensity of the signal characteristics determined based on signal intensity as a function of frequency; and the analysis of the change in the signal characteristics of the received acoustic signal in mixed time-frequency-domain includes determination of a third pattern of changes in mixed time-frequency signal intensity of the signal characteristics of the received acoustic signal from the baseline signal characteristics, the mixed time-frequency signal intensity of the signal characteristics determined based on signal intensity as a function of frequency and time; and identifying, by the one or more processors, the change to the structure based on the analyses of the change in the signal characteristics of the received acoustic signal in time-domain, in frequency-domain, and in mixed time-frequency-domain, wherein the identification of the change to the structure based on the analyses of the change in the signal characteristics of the received acoustic signal in time-domain, in frequency-domain, and in mixed time-frequency-domain includes identification of a type or a cause of the change to the structure based on the first pattern of changes in time delay and/or phase shift of the signal characteristics, the second pattern of changes in frequency-domain signal intensity of the signal characteristics, and the third pattern of changes in mixed time-frequency signal intensity of the signal characteristics.

9. The method of claim 8, wherein the set of analytic techniques includes:

for the analyses of the change in the signal characteristics of the received acoustic signal in time-domain, a time-shift mean technique, a time-shift standard deviation technique, and/or a piecewise phase correction technique;

for the analyses of the change in the signal characteristics of the received acoustic signal in frequency-domain, a time-integrated mean technique and/or a time-integrated standard deviation technique; and for the analyses of the change in the signal characteristics of the received acoustic signal in mixed time-frequency-domain, a short-time-Fourier-transform difference maximum technique, an auto-correlation mean technique, and/or an auto-correlation standard deviation technique.

10. The method of claim 8, wherein the type or the cause of the change to the structure includes material loss, material conversion, or material addition.

11. The method of claim 10, wherein the material loss includes pitting, cracking, or fracturing of the structure, the material conversion includes corrosion of the structure, and the material addition includes material migration, material accumulation, or material adsorption.

12. The method of claim 1, wherein the identification of the type or the cause of the change to the structure includes classification of the type or the cause of the change to the structure, the classification of the type or the cause of the change associated with a confidence level.

13. The method of claim 8, wherein the structure includes a metallic, rigid structure.

14. The method of claim 13, wherein the metallic, rigid structure includes a pipe, a vessel, or a container.

* * * * *